United States Patent
Berk et al.

(10) Patent No.: US 9,670,259 B2
(45) Date of Patent: Jun. 6, 2017

(54) METHOD OF INHIBITING ANGIOGENESIS USING INHIBITORS OF G-PROTEIN-COUPLED RECEPTOR KINASE INTERACTING PROTEIN-1 (GIT1)

(71) Applicants: Bradford C. Berk, Pittsford, NY (US); Jinjiang Pang, Rochester, NY (US); Syamantak Majumder, Rochester, NY (US)

(72) Inventors: Bradford C. Berk, Pittsford, NY (US); Jinjiang Pang, Rochester, NY (US); Syamantak Majumder, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 14/775,936

(22) PCT Filed: Mar. 14, 2014

(86) PCT No.: PCT/US2014/028465
§ 371 (c)(1),
(2) Date: Sep. 14, 2015

(87) PCT Pub. No.: WO2014/152971
PCT Pub. Date: Sep. 25, 2014

(65) Prior Publication Data
US 2016/0024163 A1    Jan. 28, 2016

Related U.S. Application Data

(60) Provisional application No. 61/781,832, filed on Mar. 14, 2013.

(51) Int. Cl.
| | | |
|---|---|---|
| C07K 14/47 | (2006.01) | |
| A61K 38/10 | (2006.01) | |
| A61K 38/16 | (2006.01) | |
| A61K 38/17 | (2006.01) | |
| A61K 39/395 | (2006.01) | |
| A61K 47/48 | (2006.01) | |
| C07K 16/28 | (2006.01) | |

(52) U.S. Cl.
CPC .......... *C07K 14/4722* (2013.01); *A61K 38/10* (2013.01); *A61K 38/16* (2013.01); *A61K 38/1709* (2013.01); *A61K 39/3955* (2013.01); *A61K 47/48346* (2013.01); *C07K 16/28* (2013.01)

(58) Field of Classification Search
CPC .... C07K 14/4722; C07K 16/28; A61K 38/10; A61K 38/16; A61K 38/1709; A61K 39/3955; A61K 47/48346
See application file for complete search history.

(56) References Cited

U.S. PATENT DOCUMENTS 7,838,490 B2    11/2010  Schwarz et al.
7,994,130 B2 *   8/2011  Li .................... C07K 14/70503
                                                    514/1.1

FOREIGN PATENT DOCUMENTS

WO        02/086122 A2    10/2002
WO     WO2009033803    *    3/2009

OTHER PUBLICATIONS

Blanes-Mira C, et al. Int. J. Cosmet. Sci. 24(5):303-301. Oct. 2002. Available online at—doi: 10.1046/j.1467-2494.2002.00153.x.*
Pang J, et al. Circulation. 118(18):Suppl. 2. S462. Oct. 28, 2008.*
Pang J, et al. Circulation. 119(11):1524-1532. Mar. 24, 2009. Available online at—DOI: 10.1161/CIRCULATIONAHA.108. 823997.*
Pang J, et al. Circulation 122:Suppl. 21. Nov. 23, 2010.*
UniProt Q9Y2X7, GIT1_HUMAN (2013).
Pang et al., "G-Protein-Coupled Receptor Kinase Interacting Protein-1 Is Required for Pulmonary Vascular Development," Circulation 119:1524-1532 (2009).
Majumder et al., "G-Protein-Coupled Receptor-2-Interacting Protein-1 Is Required for Endothelial Cell Directional Migration and Tumor Angiogenesis Via Cortactin-Dependent Lamellipodia Formation," Arterioscler Throm Vasc Biol. 34:419-426 (2013).
Wang et al., "GIT1 Regulates Angiogenesis by Affecting Endothelial Cell Podosome Formation and Migration," Circulation 116:II_81 (2007) (Abstract only).
International Search Report and Written Opinion corresponding to PCT/US2014/028465 mailed Nov. 12, 2014.

* cited by examiner

*Primary Examiner* — Robert Landsman
(74) *Attorney, Agent, or Firm* — LeClairRyan, a Professional Corporation

(57) ABSTRACT

The present invention is directed to methods and compositions comprising G-protein-coupled receptor kinase interacting protein-1 (GIT1) inhibitors that are suitable for inhibiting angiogenesis in a subject and treating related conditions.

13 Claims, 17 Drawing Sheets

```
Human         132  dlskqlhss vrtgnletcl rllslgaqan ffhpekgttp lhvaakagqt lqaellvvyg  190
Mouse         132  dlskqlhss vrtgnletcl rllslgaqan ffhpekgttp lhvaakagqt lqaellvvyg  190
Rat           132  dlskqlhss vrtgnletcl rllslgaqan ffhpekgttp lhvaakagqt lqaellvvyg  190
Chick         132  dlskqlhss vrtgnletcl rllslgaqan ffhpekgttp lhvaakagqi lqaellvvyg  190
Drome         182  elsrqlhas vrtsnletsl rflvqgadpn yyhedklstp lhmaakfgqa sqiemlliyg  240

Consensus 1     1  XLSXQLHXS VRTXNLETXL RXLXXGAXXN XXHXXKXXTP LHXAAKXGQX XQXEXLXXYG   59
Consensus 2     1  DLSKQLHSS VRTGNLETCL RLLSLGAQAN FFHPEKGTTP LHVAAKAGQX LQAELLVVYG   59
w/out Drome Human         191  adpgspdvng rtpidyarqa ghhelaerlv ecqyeltd   228    (SEQ ID NO:2)
Mouse         191  adpgspdvng rtpidyarqa ghhelaerlv ecqyeltd   228    (SEQ ID NO:3)
Rat           191  adpgspdvng rtpidyarqa ghhelaerlv ecqyeltd   228    (SEQ ID NO:4)
Chick         191  adpgapdvng rtpidyarqa aqhelaerlv ecqyeltd   228    (SEQ ID NO:5)
Drome         241  advnaldgng mtplelaran nhntiaerll damydvtd   278    (SEQ ID NO:6)

Consensus 1    60  ADXXXXDXNG XTPXXXARXX XXXXXAERLX XXXXYXXTD    97    (SEQ ID NO:7)
Consensus 2    60  ADPGXPDVNG RTPIDYARQA XXHELAERLV ECQYELTD     97    (SEQ ID NO:8)
```

METHOD OF INHIBITING ANGIOGENESIS USING INHIBITORS OF G-PROTEIN-COUPLED RECEPTOR KINASE INTERACTING PROTEIN-1 (GIT1)

This application is a national stage application under 35 U.S.C. §371 of PCT Application No. PCT/US2014/028465, filed Mar. 14, 2014, which claims the benefit of U.S. Provisional Patent Application Ser. No. 61/781,832, filed Mar. 14, 2013, which is hereby incorporated by reference in its entirety.

This invention was made with government support under grant number HL63462 awarded by National Institutes of Health. The government has certain rights in this invention.

FIELD OF THE INVENTION

The present invention relates to inhibitors of G-protein-coupled receptor kinase interacting protein-1 (GIT1) suitable for the modulation of angiogenesis and related conditions.

BACKGROUND OF THE INVENTION

Sprouting angiogenesis is required for new vessel formation during both development and wound repair (Carmeliet et al., *Nature* 436:193 (2005); Gerhardt et al., *J Cell Biol.* 161:1163 (2003)). VEGF mediated phospholipase C gamma (PLCγ) activation is essential for endothelial cell (EC) migration, proliferation and tube formation. This pathway is regarded as the canonical signaling pathway during angiogenesis. Recently, it was found that another essential process for angiogenesis is endothelial cell sprouting by filopodia that sense and respond to VEGF gradients (Gerhardt et al., *J Cell Biol.* 161:1163 (2003); Ruhrberg et al., *Genes Dev.* 16:2684 (2002); West et al., *Development* 132:1855 (2005)). Formation of a vascular plexus requires temporary spatial differentiation of endothelial cells into tip and stalk cells, a behavior that is tightly regulated by VEGF-Notch1-delta like 4 (Dll4) signaling (Artavanis-Tsakonas et al., *Science* 284:770 (1999); Phng et al., *Dev. Cell* 16:196 (2009); Lobov et al., *Proc. Natl. Acad. Sci.* 104:3219 (2007)). Many aspects of the signal pathway have been elucidated. However, the feedback regulation that controls tip and stalk cell behavior has not been described.

The major phenotype of the G-protein-coupled receptor (GPCR)-kinase interacting protein-1 (GIT1) knock out (KO) mouse is defective pulmonary vascular development (Pang et al., *Circulation* 1524 (2009)). Endothelial cell (EC) function in response to VEGF was significantly impaired as demonstrated by decreased proliferation, tube formation and activation of VEGF mediated PLCγ activation. Interestingly, other vascular beds of GIT1 KO mice were normal except the retina. As both murine retina and lung vascular development occur postnatally, these results suggest a unique role for GIT1 in postnatal angiogenesis (Hislop et al., *Paediatr. Respir. Rev.* 6:35 (2005)).

The present invention is directed to overcoming these and other deficiencies in the art.

SUMMARY OF THE INVENTION

A first aspect of the present invention relates to a method of inhibiting angiogenesis in a subject. This method includes administering a G-protein-coupled receptor kinase interacting protein-1 (GIT1) inhibitor to the subject under conditions effective to inhibit angiogenesis in the subject.

A second aspect of the invention relates to an isolated peptide comprising the amino acid sequence of SEQ ID NO: 7 or a fragment thereof.

Abnormal angiogenesis underlies and controls the progression of a wide variety of different disease states. For example, abnormal angiogenesis promotes tumor growth, macular degeneration, and pulmonary arterial hypertension. Agents that effectively turn off the endogenous signaling pathways controlling angiogenesis are valuable therapeutic agents suitable for the treatment of these conditions. As described herein the GIT1 ankyrin repeat domain and spa2 homology domain (SHD) are critical regulatory domains of angiogenesis. Accordingly, GIT1 inhibitors, such as ankyrin domain and SHD derived peptides, are therapeutic agents useful for inhibiting angiogenesis in conditions mediated by abnormal angiogenesis.

BRIEF DESCRIPTION OF THE DRAWINGS

FIGS. 1A-1D show whole mount isolectin B4 staining of retinas of GIT1wildtype (WT) and KO mice at P5. FIGS. 1E-1H show compromised growth of the retina vasculature in GIT1 KO mice. Reduced branch points in the vascular plexus (compare FIGS. 1E (WT) and 1F (KO)) and decreased tip cells and filopodia extensions (compare FIGS. 1G (WT) and 1H (KO)) in the sprouting area of GIT1 KO mice (Higher-magnification images of the boxed regions are shown in FIGS. C and D, respectively) are also shown. FIGS. 1I-1K demonstrate that GIT1 is highly expressed in the leading edge of the growing capillary plexus at P5. GIT1 was detected with rabbit polyclonal GIT1 antibody and goat-anti-rabbit Alexa-586. Vessels were stained by FITC-isolectin B4. The merged image showed that GIT1 was highly expressed in the leading edge of retina vasculature (FIG. 1K). FIGS. 1L-1O show quantification of vessel length (FIG. 1L), branch points (FIG. 1M), tip cells density (FIG. 1N) and filopodia extensions (FIG. 1O) of vessels. *$P<0.05$ compared with WT group of the same time point (mean±SE; n=8).

FIG. 2B shows quantitation of relative changes of GIT1 protein (normalized to GAPDH). *$P<0.05$ compared with P5 group (mean±SE; n=5).

FIGS. 3A-3B are representative micrographs of sprouting microvessels from an aortic ring grown in the presence of 50 ng/ml VEGF for 9 days. Scale bars, 200 µm. FIGS. 3C-3E are bar graphs showing the quantitative assessment of sprouting length (FIG. 3C), sprouting area (FIG. 3D) and tip cell numbers (FIG. 3E) in WT and GIT1 KO mice.

FIG. 4A is a diagram of the strategy used to generate conditional GIT1 KO mice. FIG. 4B is a representative Southern blot identifying an ES colony with incorporation of the "conditional" recombination vector, as indicated by the 3.4 kb band. Isolated DNA was digested with Xba I and EcoR I, separated by electrophoresis in a 0.7% agarose gel, transferred to a membrane, and probed with a DNA fragment consisting of a region of the first Git1 intron. The flanking lanes demonstrate the wild-type genotype. FIG. 4C is a western blot showing expression of GIT1 in lung tissues of Git1$^{f/f:Tie2-Cre-}$ (endothelial cell specific GIT1 WT mice) and Git1$^{f/f:Tie2-Cre+}$ mice⁻ (endothelial cell specific GIT1 KO mice).

FIGS. 5A-5F are images of whole mount Isolectin B4 staining in retinas of Git1$^{f/f:Tie2-Cre-}$ and Git1$^{f/f:Tie2-Cre-}$ mice at P5. The compromised growth of the retina vasculature in Git1$^{f/f:Tie2-Cre+}$ mice is shown in FIGS. 5A-5B. FIGS. 5C-5F are higher magnification images of the boxed regions in FIGS. A and B, respectively. A reduction in branch points in the vascular plexus is shown in FIGS. 5C-5D, and a decrease in tip cell and filopodia extension in the sprouting area is shown in FIGS. 5E-5F. FIGS. 5G-5J are bar graphs showing quantitation of vessel length (FIG. 5G), branch points (FIG. 5H), tip cell density (FIG. 5I) and filopodia extensions (FIG. 5J). *P<0.05 compared with Git1$^{f/f:Tie2-Cre-}$ group of same time point (mean±SE; n=6).

FIGS. 6A and 6C are western blots showing the increase in Dll4 expression in retina and lung tissue, respectively, from GIT1 KO mice. Tissues of GIT WT and GIT1 KO mice at P5 were isolated and expression of Dll4 was assayed by western blot. Quantification of the relative changes of Dll4 expression in retina and lung tissue (normalized to GAPDH, *P<0.05 compared to WT groups; mean±SE; n=3) is shown in the bar graphs in FIGS. 6B and 6D, respectively. FIGS. 6E-6I show that Dll4 and Hey1 mRNA expression increased after GIT1 depletion with siRNA. HUVECs were transfected with GIT1 and control siRNA for 48 h. Dll4 and Hey1 mRNA and protein expression were detected by real-time quantitative reverse transcription-PCR (qRT-PCR) and western blot (FIG. 6G). Quantified relative changes of Dll4 and Hey1 mRNA expression (normalized to actin; *P<0.05 compared with control siRNA group (mean±SE; n=3)) and protein expression are shown in bar graphs in FIGS. 6E-6F and 6H-6I, respectively. FIG. 6J shows that N1-ICD was increased after GIT1 depletion with siRNA. Notch1 cleavage was detected by N1-ICD antibody. There was no change of total Notch1 expression. Quantification of cleaved Notch1 (Normalized to total Notch1 *P<0.05 compared with control siRNA groups; mean±SE; n=3) is shown in a bar graph in FIG. 6K.

FIGS. 8A-8B show GIT1 localizes to both cytoplasm and nucleus. HUVECs were washed, fixed and stained using GIT1 antibody (FIG. 8A). Cell fractionation was also performed on HUVECs (FIG. 8B). FIG. 8C shows GIT1 associates with RBP-J. The association of endogenous GIT1 and RBP-J in HUVECs was assayed by immunoprecipitation (IP) with RBP-J antibody and probed with GIT1. FIGS. 8D-8E show GIT1 inhibits Notch signaling through GIT1(1-250). The functional domains of GIT1 are illustrated in FIG. 8D. In FIG. 8E, HEK 293 cells were cotransfected with GIT1WT or the shown truncation mutants together with Hey1 luciferase reporter gene, N1-ICD and β-galactosidase (β-gal). After transfection for 18 h, luciferase and β-gal activities were measured. FIGS. 8F-8G show GIT1 (ANK) competes with N1-ICD to bind to RBP-J. In FIG. 8F, HEK293 cells were transfected with GFP-GIT1 (WT), GFP-GIT1(ΔANK) or GFP-GIT1(ANK). The interaction of RBP-J and GIT1 mutants was assayed by immunoprecipitation with GFP antibody and probing for RBP-J. In FIG. 8G, HEK293 cells were transfected with pcDNA or GFP-GIT1(ANK) and N1-ICD. The interaction of RBP-J and N1-ICD was assayed by immunoprecipitation with RBP-J antibody and probing for N1-ICD. Lower panel showed expression of N1-ICD and GFP-GIT1(ANK) in total cell lysis (TCL). FIG. 8H shows that the ankyrin repeat domain is responsible for GIT1 in Notch signaling. HEK 293 cells were cotransfected with GIT1WT or its mutants together with Hey1 luciferase reporter gene, N1-ICD and β-gal. After transfection for 18 h, luciferase and β-gal activities were detected. FIGS. 8I-8M show GIT1(ANK) rescues the defective tube formation caused by GIT1 depletion. HUVECs were co-transfected with GFP or GFP-GIT1 (ANK) together with control siRNA or GIT1 siRNA. After transfection for 24 h, the cells were re-seeded in a 96 well plate coated with Matrigel and stimulated with VEGF (50 ng/ml) for 18 h. Representative images are shown in FIGS. 8I-8L. Bar=200 μm. The formed tubes in each group were quantified (n=4) (FIG. 8M).

FIG. 9 is an alignment of GIT1 ankyrin repeat domain sequences derived from human (SEQ ID NO: 2), mouse (SEQ ID NO: 3), rat (SEQ ID NO: 4), chick (SEQ ID NO: 5), and drome (SEQ ID NO: 6) GIT1 amino acid sequences. The GIT1 peptide of SEQ ID NO: 7 is a GIT1 ankyrin repeat domain consensus sequence based on the alignment of SEQ ID NOs: 2-6, and the GIT1 peptide of SEQ ID NO: 8 is a GIT1 ankyrin repeat domain consensus sequence based on the alignment of SEQ ID NOs: 2-5.

FIG. 12C is a schematic illustrations of how GIT1-SHD is acting as a specific PLCγ inhibitor in canonical VEGF signaling. GIT1-SHD competes with endogenous GIT1 to bind to PLCγ, which inhibits VEGF induced PLCγ phosphorylation (Y783). This leads to decreased angiogenesis by inhibition of EC proliferation, migration and tube formation.

Figures 13A, 13B:
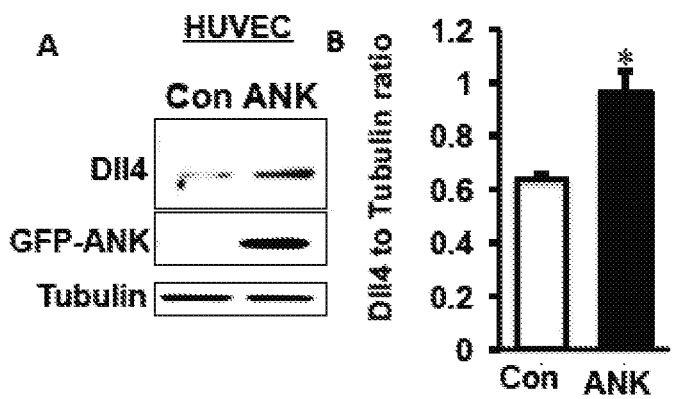

FIGS. 13A-13B show that ANK lentivirus increases Dll4 protein expression in HUVEC. In FIG. 13A, HUVECs were treated with Lenti-vector (control, con) or Lenti-ANK (ANK) for 24 hour. Dll4 protein expression was detected by western blot. FIG. 13B is a graph quantifying Dll4 protein expression (normalized to Tubulin). *P<0.05 compared with Lenti-vector group (mean±SE; n=3).

Figures 14A, 14B, 14C, 14D, 14E:
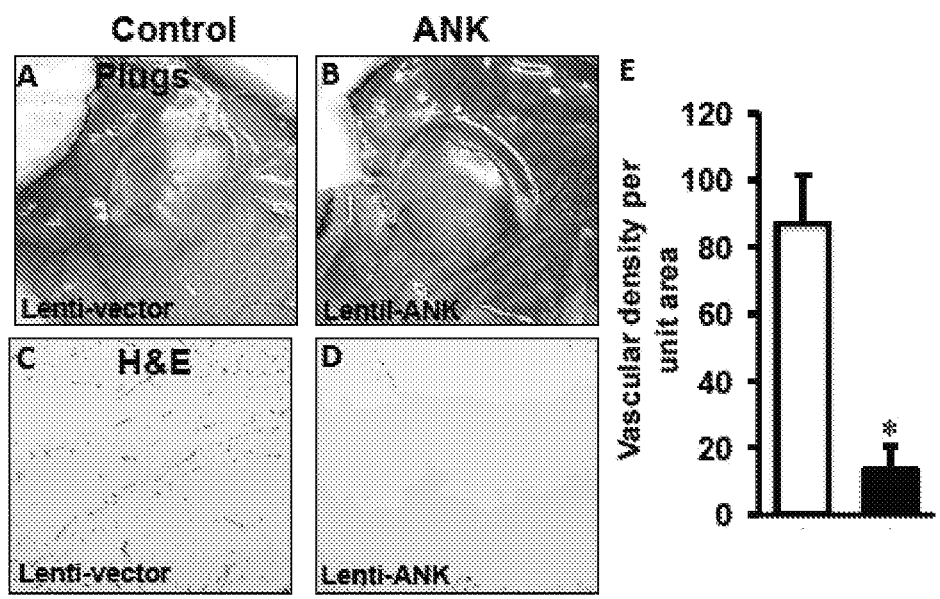
Figures 15A, 15B, 15C, 15D, 15E, 15F, 15G, 15H:
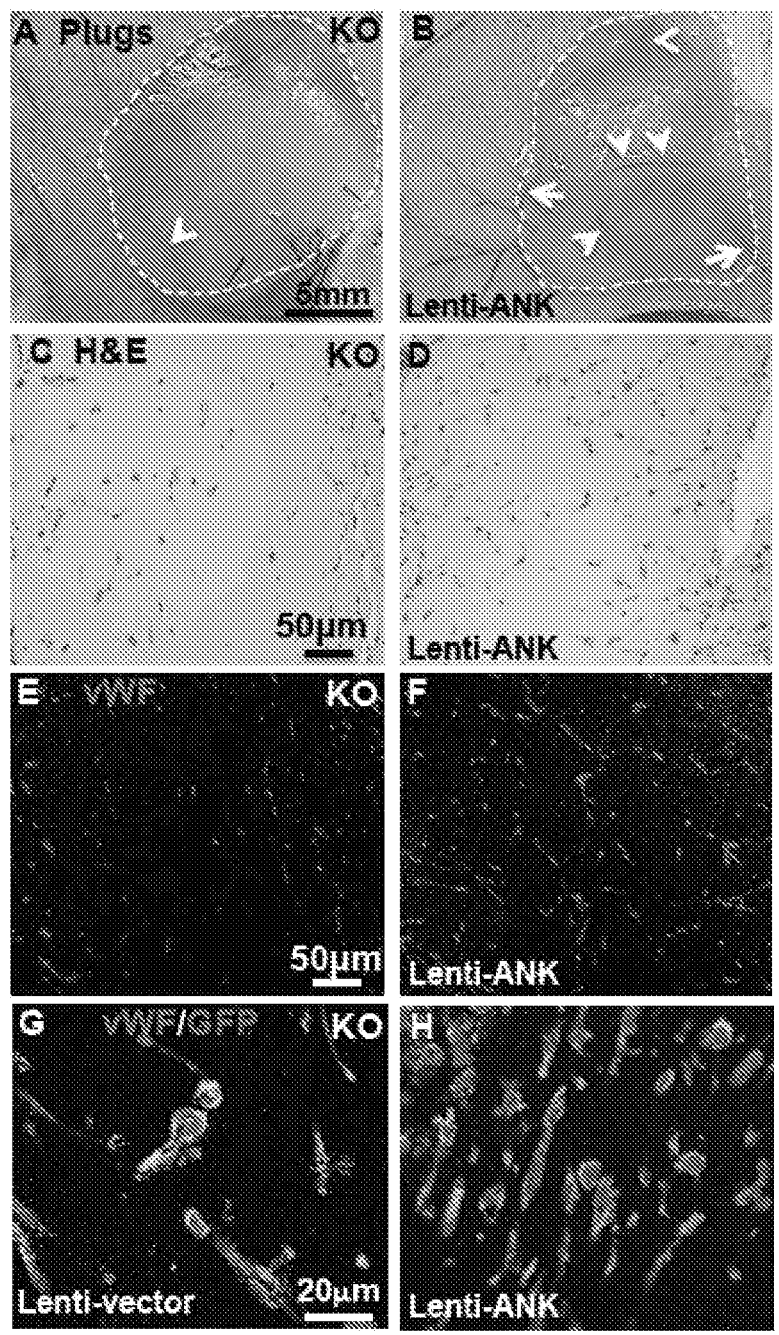
Figure 15I:
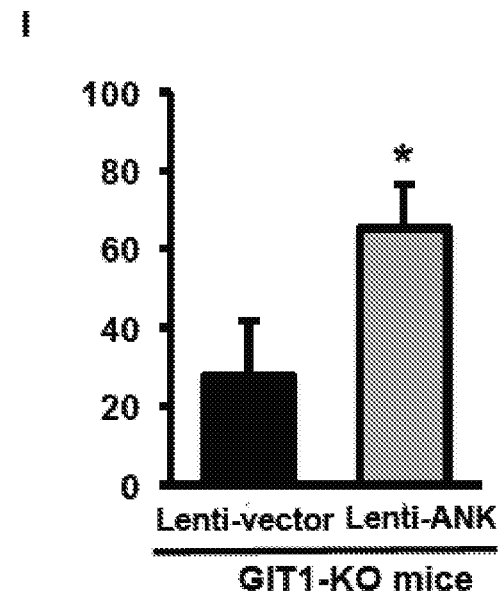

FIGS. 14A-14E show ANK lentivirus inhibits angiogenesis in GIT1-WT mice. The Matrigel plugs shown in FIGS. 14A and 14B were generated by subcutaneous injection of 250 µl matrigel containing lentivirus GFP and lenti-GFP ANK in GIT1-WT mice. Plugs were harvested, fixed and embedded in paraffin. FIGS. 14C-14D are images of cells in the plug stained for hematocylin and eosin. FIG. 14E is a graph quantifying vessel density in plugs as measured by counting vessel numbers per field (n=4). *P<0.05 compared with Lenti-vector group FIGS. 15A-15I show that ANK lentivirus restores impaired angiogenesis in GIT1-KO mice in vivo. FIGS. 15A-15B are photomicrographs of Matrigel plugs that were generated by subcutaneous injection of 250 µl matrigel containing lentivirus GFP and lenti-GFP ANK in GIT1-KO mice. Plugs were harvested, fixed and embedded in paraffin. Cells in the plug were stained for hematocylin and eosin as shown in the photomicrographs of FIGS. 15C-15D. Endothelial cells were stained by Von Willebrand factor (VWF, an endothelial cell marker) as shown in the fluorescent photomicrographs of FIGS. 15E-15H. Vessel density was measured by counting vessel numbers per field (n=6) (FIG. 15I). *P<0.05 compared to Lenti-vector group.

Figures 16A, 16B:
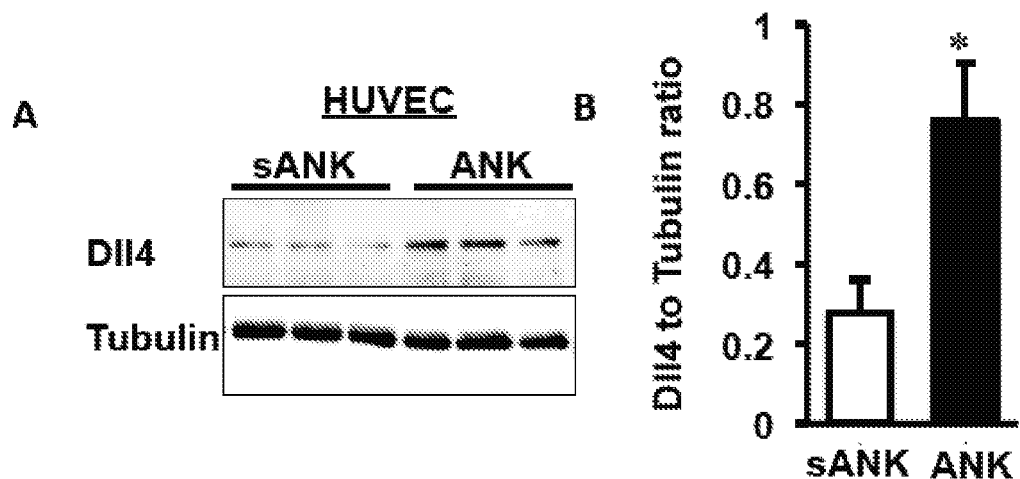

FIGS. 16A-16B show ANK peptide increases Dll4 protein expression in HUVECs. HUVECs were treated with sANK and ANK peptide (15 µM) for 24 hours. Dll4 protein expression was detected by western blot as shown in FIG. 16A. Quantitation of Dll4 protein expression (normalized to Tubulin) is shown in the graph of FIG. 16B. *P<0.05 compared to sANK peptide group (mean±SE; n=3).

Figures 17A, 17B, 17C:
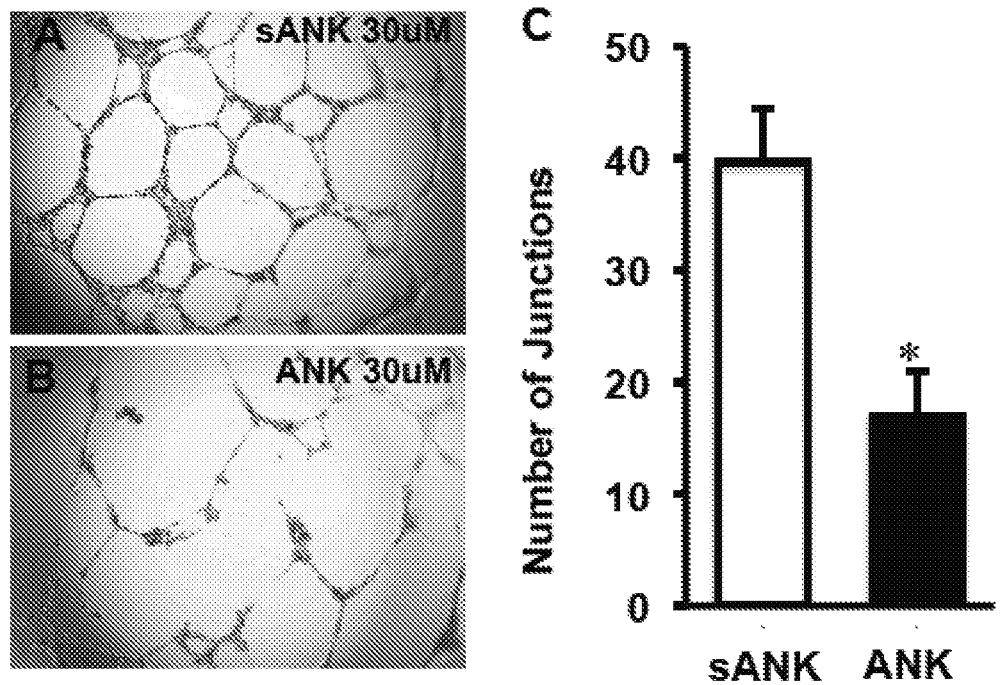

FIGS. 17A-17C show that ANK peptide inhibits VEGF induced tube formation in HUVECs. HUVECs at P4 were seeded in Matrix gel (VEGF, 10 ng/mL) and treated with sANK or ANK peptide (15 µM) for 16 hours. Tube formation was imaged (FIGS. 17A and 17B) and the number of junctions were analyzed (FIG. 17C). *P<0.05 compared to sANK peptide group (mean±SE; n=3).

Figures 18A, 18B, 18C, 18D:
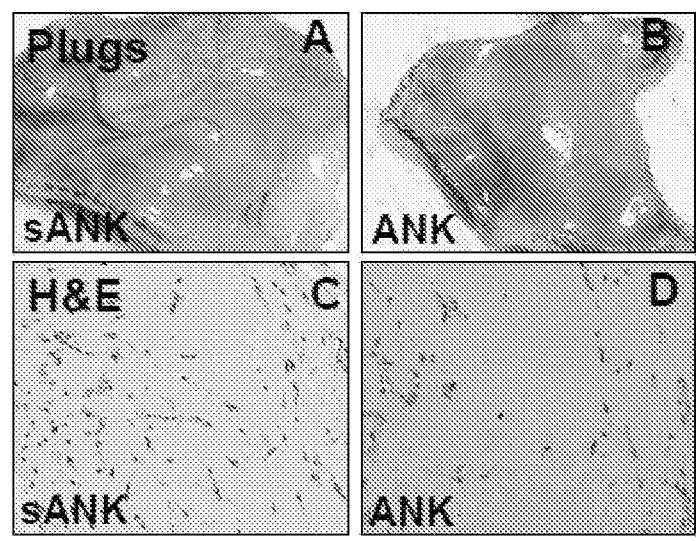

FIG. 18A-18D demonstrate ANK peptide inhibition of angiogenesis in vivo. Matrigel plugs shown in FIGS. 18A and 18B were generated by subcutaneous injection of 250 µl matrigel containing 75 µM of sANK (FIG. 18A) or ANK (FIG. 18B) in C57 mice. Plugs were harvested, fixed and embedded in paraffin. Cells in the plug were stained for hematocylin and eosin as shown in FIGS. 18C (sANK) and 18D (ANK).

Figures 19A, 19B:
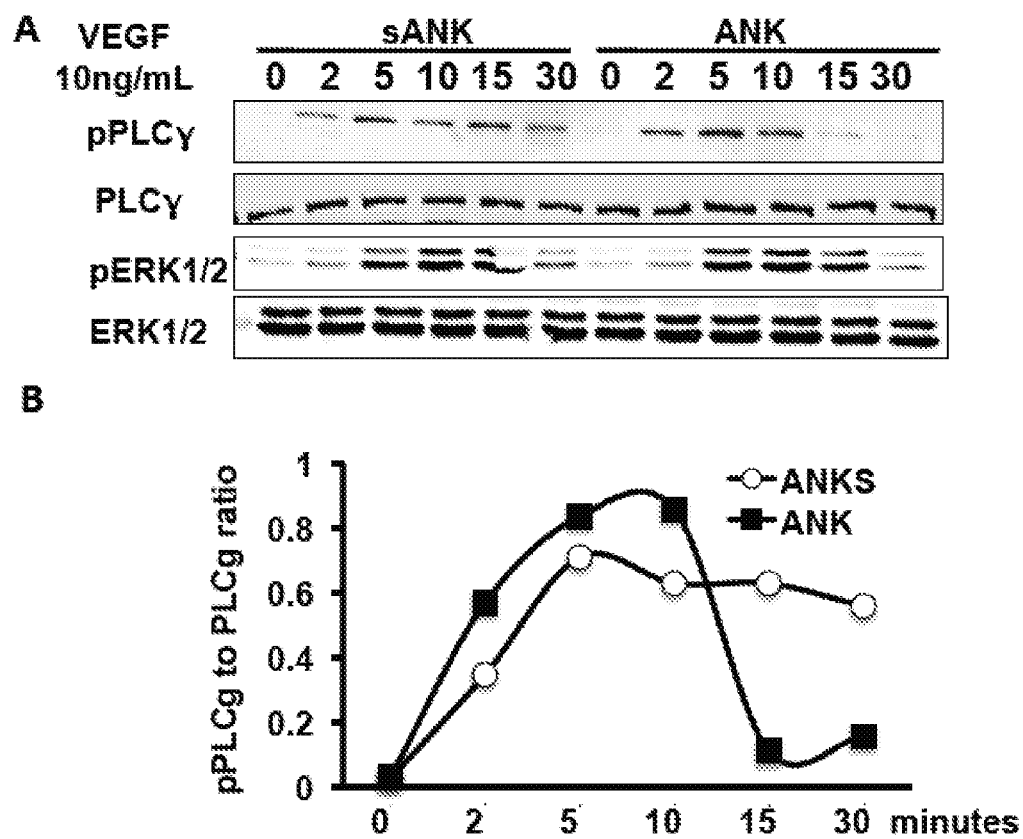

FIG. 19A-19B show that ANK peptides inhibit VEGF induced PLCγ activation in HUVEC. HUVECs at P4 were plated on 6 well tissue culture plate and grown overnight. The following day, cells were treated with 15 µM of sANK and ANK peptide for 4 hour in low serum media. After 4 hours, cells were stimulated with 10 ng/mL of VEGF for different time points. Cells were lysed for western blot analysis to measure ERK1/2 and PLCγ activation (FIG. 19A). Quantitation of the western blot data of FIG. 19A is depicted in the graph of FIG. 19B.

DETAILED DESCRIPTION OF THE INVENTION

A first aspect of the present invention relates to a method of inhibiting angiogenesis in a subject. This method involves selecting a subject having a condition associated with abnormal angiogenesis and administering a G-protein-coupled receptor kinase interacting protein-1 (GIT1) inhibitor to the selected subject under conditions effective to inhibit angiogenesis in the subject.

In accordance with this aspect of the present invention, the subject has a condition associated with abnormal angiogenesis, i.e., a condition associated with increased or enhanced angiogenesis. Conditions associated with abnormal angiogenesis include, without limitation, cancer, metastatic cancer, macular degeneration, and pulmonary arterial hypertension.

As used herein, "subject" refers to any animal, preferably a mammal, that is amenable to treatment in accordance with the methods of the present invention. Preferably, the subject is a mammal. Exemplary mammalian subjects include, without limitation, humans, non-human primates, dogs, cats, rodents (e.g., mouse, rat, guinea pig), horses, cattle and cows, sheep, and pigs.

GIT1 is a multi-domain scaffold protein that binds to the G-protein coupled receptor kinase-2 (GRK2) and plays a role in many cellular functions including receptor internalization, focal adhesion remodeling, and signaling pathways of both G-protein coupled receptors (GPCRs) and tyrosine kinase receptors. The full-length GIT1 protein has an N-terminal ARF GTPase activating protein domain, three ankyrin repeats, a Spa2-homology domain (SHD), a coiled-coil domain and a paxillin-binding site (PBS). The full-length amino acid sequence of human GIT1 is provided below as SEQ ID NO: 1

```
  1 msrkgpraev cadcsapdpg wasisrgvlv cdeccsvhrs lgrhisivkh lrhsawpptl 61 lqmvhtlasn gansiwehsl ldpaqvqsgr rkanpqdkvh piksefirak yqmlafvhkl 121 pcrdddgvta kdlskqlhss vrtgnletcl rllslgaqan ffhpekgttp lhvaakagqt 181 lqaellvvyg adpgspdvng rtpidyarqa ghhelaerlv ecqyeltdrl afylcgrkpd 241 hknghyiipq madsldlsel akaakkklqa lsnrlfeela mdvydevdrr endavwlatq 301 nhstivters avpflpvnpe ysatrnqgrq klarfnaref atliidilse akrrqqgksl 361 ssptdnlels lrsqsdlddq hdydsvasde dtqeplrst gatrsnrars mdssdlsdga 421 vtlqeylelk kalatseakv qqlmkvnssl sdelrrlqre ihklqaenlq lrqppgpvpt
```

```
-continued
481 pplpseraeh tpmapggsth rrdrqafsmy epgsalkpfg gppgdelttr lqpfhstele 541 ddaiysvhvp aglyrirkgv sasavpftps spllscsqeg srhtsklsrh gsgadsdyen 601 tqsgdpllgl egkrflelgk eedfhpeles ldgdldpglp stedvilkte qvtkniqell 661 raagefkhds fvpcsekihl avtemaslfp krpalepvrs slrllnasay rlqsecrktv 721 ppepgapvdf qlltqqviqc aydiakaakq lvtittrekk q
```

As demonstrated herein, GIT1 is an important regulator of angiogenesis via its role in mediating the VEGFR-Notch1-Delta like ligand 4 (Dll4) signaling pathway. Specifically, GIT1 competes with Notch binding to recombining binding protein suppressor of hairless (RBP-J) via its ankyrin repeat domain to enhance angiogenesis.

In one embodiment of this aspect of the present invention, the GIT1 inhibitor is a GIT1 inhibitory peptide. One class of suitable GIT1 inhibitor peptides include peptides comprising the ankyrin repeat domain of GIT1 or any portion thereof. These peptides serve as "blocking peptides", blocking GIT1 protein from binding to RBP-J, thereby inhibiting angiogenesis. Accordingly, peptides comprising the ankyrin repeat domain or a portion thereof, are useful for inhibiting angiogenesis in subjects having a condition associated with impaired angiogenesis.

The ankyrin repeat domain of GIT1 spans amino acid residues 132-228 of the full-length human GIT1 amino acid sequence of SEQ ID NO: 1 (shown below as SEQ ID NO: 2).

```
                                        (SEQ ID NO: 2)
kdlskqlhss vrtgnletcl rllslgagan ffhpekgttp lhvaakagqt lqaellvvyg adpgspdvng rtpidyarqa ghhelaerlv ecqyeltd
```

The ankyrin repeat domain ("ANK") of GIT1 is highly conserved across various species, including mouse, rat, chick, and drome as demonstrated by the sequence alignment shown in FIG. 9. Accordingly, in one embodiment of the present invention, a therapeutically useful GIT1 inhibitory peptide comprises an amino acid sequence of SEQ ID NO: 7, or an RBP-J binding fragment thereof. SEQ ID NO: 7 is a consensus GIT1 ANK peptide generated from the alignment of the SEQ ID NOs: 2-6, where X is any amino acid residue. In another embodiment of the present invention, a therapeutically useful GIT1 ANK peptide comprises the amino acid sequence of SEQ ID NO: 8, or an RBP-J binding fragment thereof. SEQ ID NO: 8 is a consensus GIT1 ANK peptide generated from the alignment of the SEQ ID NOs: 2-5, where X is any amino acid residue peptide. In yet another embodiment of the present invention, a therapeutically useful GIT1 ANK peptide comprises an amino acid sequence of SEQ ID NO: 2, or an RBP-J binding fragment thereof. In yet another embodiment of the present invention, a therapeutically useful GIT1 ANK peptide comprises an amino acid sequence selected from the amino acid sequences of SEQ ID NOs: 3-6.

It is to be understood that the present invention contemplates the use of any mammalian or non-mammalian GIT1 ANK peptide sequence corresponding to the GIT1 ANK peptide of SEQ ID NO: 2 above. Homologous GIT1 peptides from mammals and non-mammals other than those described above are preferably characterized by an amino acid identity of at least about 60 percent, more preferably at least about 70 percent or 80 percent, most preferably at least about 85 percent or 90 percent or 95 percent as compared to human GIT1 ANK peptide of SEQ ID NO: 2.

As noted above, there are three ANK repeats within the ANK domain of the GIT1 amino acid sequence, and smaller peptides comprising any one of the individual ANK repeats are considered to be therapeutically useful GIT1 inhibitory peptides in accordance with this aspect of the present invention. Accordingly, a suitable therapeutic GIT1 peptide comprises an amino acid sequence corresponding to the first ANK repeat, i.e., residues 1-30 of SEQ ID NOs: 7 or 8, including amino acid residues 132-161 of SEQ ID NO:1 or residues 1-30 of SEQ ID NO: 2 (DLSKQLHSSVRTGN-LETCLRLLSLGAQANF). A suitable therapeutic GIT1 peptide may also comprise an amino acid sequence corresponding to the second ANK repeat which spans residues 35-64 of SEQ ID NOs:7 or 8, including amino acid residues 166-195 of SEQ ID NO: 1 or residue 35-64 of SEQ ID NO: 2 (KGTTPLHVAAKAGQTLQAELLVVYGADPGS). A suitable GIT1 therapeutic ANK peptide may also include a fragment of the second ANK repeat corresponding to amino acid residues 36-48 of SEQ ID NOs: 7 or 8, including amino acid residues 167-179 of SEQ ID NO:1 or 36-48 of SEQ ID NO:2 (GTTPLHVAAKAGQ). A suitable GIT1 therapeutic ANK peptide also comprises an amino acid sequence corresponding to the third ANK repeat which spans amino acid residues 68-97 of SEQ ID NOs: 7 or 8, including amino acid residues 199-228 of SEQ ID NO: 1 or residues 68-97 of SEQ ID NO: 2 (NGRTPIDYARQAGHHELAERLVEC-QYELTD). According to this aspect of the present invention, therapeutically useful GIT1 peptides for inhibiting angiogenesis comprise these individual ANK repeat sequences or fragments thereof.

Figures 12A, 12B, 12C:
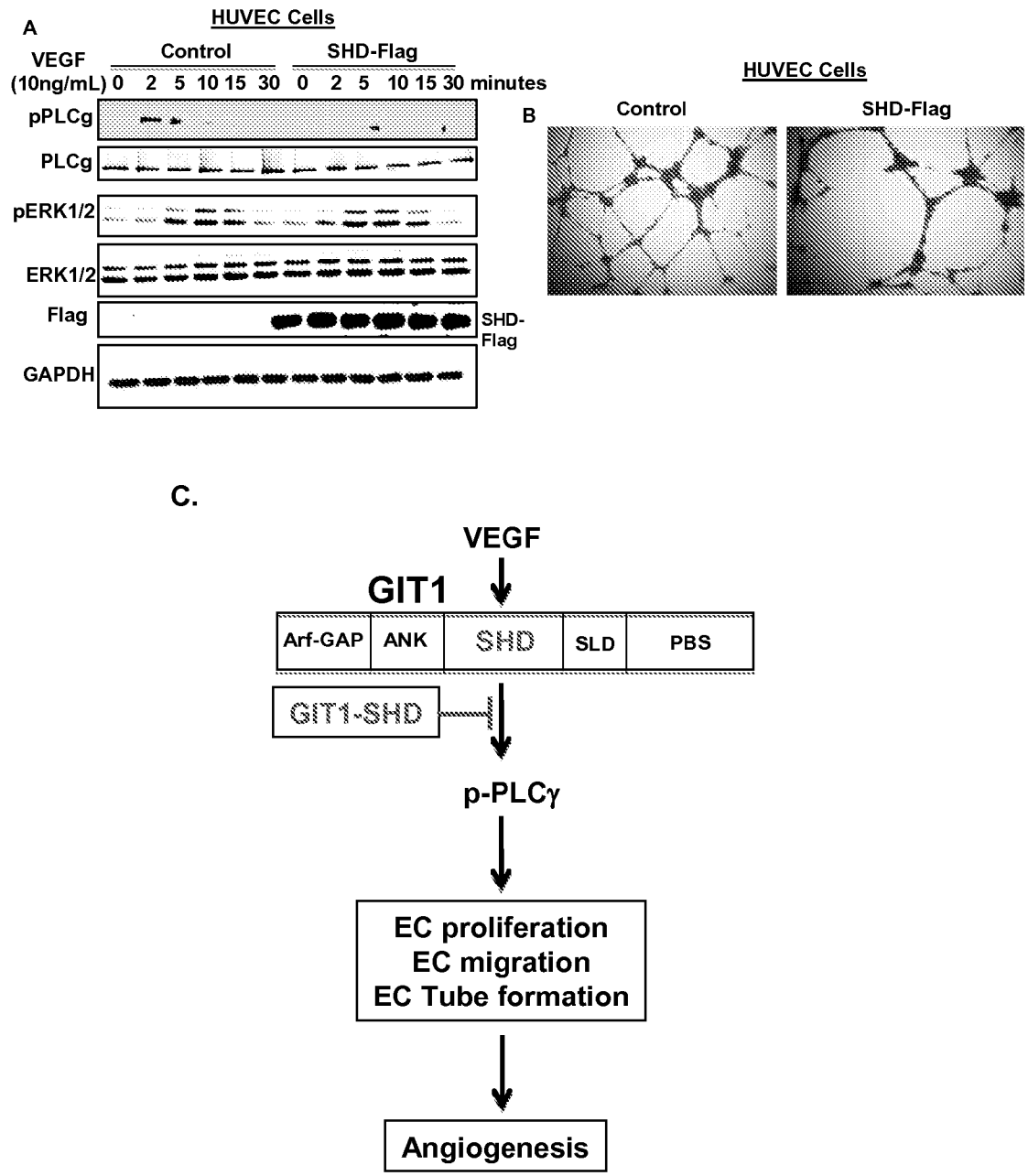
FIGS. 12A-12C demonstrate that overexpression of the spa2 homology domain (SHD) of GIT1 (i.e., residue 250-420 of SEQ ID NO:1) in human umbilical cord endothelial cells (HUVEC) inhibits VEGF mediated PLCγ activation (FIG. 12A) and EC tube formation (FIG. 12B). Overexpression of SHD had no effect on ERK1/2 activation as shown in FIG. 12A.

Other suitable GIT1 inhibitory peptides includes dominant negative GIT1 peptides that interfere with activation of GIT1-dependent signaling pathways by molecules such as VEGF. An exemplary inhibitor peptide of the present invention is a peptide that mimics a region of the SHD domain of GIT1 (i.e., amino acid residues 250-420 of SEQ ID NO: 1), which is involved in GIT1 signaling through PLCγ (see FIG. 12). Suitable inhibitor peptides derived from the SHD include, without limitation, peptides having an amino acid sequence of DLSELAKAAKKKLQALSNRLFEELAMD-VYDEVDRRENDAVWLATQNHS (SEQ ID NO: 17; corresponding to amino acid residues 256-303 of SEQ ID NO: 1) and an amino acid sequence of DQHDYDSVASDEDT-DQE (SEQ ID NO:18; corresponding to amino acid residues 379-395 of SEQ ID NO: 1).

Such inhibitory peptides may be chemically synthesized using known peptide synthesis methodology or may be prepared and purified using recombinant technology. Such peptides are usually at least about 5 amino acids in length, but can be anywhere from 5 to 100 amino acids in length. Such peptides may be identified without undue experimentation using well known techniques. Techniques for screening peptide libraries for peptides that are capable of specifically binding to a polypeptide target, in this case GIT1, are well known in the art (see e.g., U.S. Pat. No. 5,556,762 to Pinilla et al.; U.S. Pat. No. 5,750,373 to Garrard et al.; U.S. Pat. No. 4,708,871 to Geysen; U.S. Pat. No. 4,833,092 to Geysen; U.S. Pat. No. 5,223,409 to Ladner et al.; U.S. Pat. No. 5,403,484 to Ladner et al.; U.S. Pat. No. 5,571,689 to Heuckeroth et al.; U.S. Pat. No. 5,663,143 to Ley et al.; and PCT Publication Nos. WO84/03506 to Geysen and WO84/03564 to Geysen, which are hereby incorporated by reference in their entirety).

In another embodiment of this aspect of the present invention, the GIT1 inhibitor is an antibody or antigen binding portion thereof that binds to a GIT1 ankyrin repeat domain. Accordingly, a suitable antibody or antigen binding portion thereof is one that binds to at least a portion of an amino acid sequence of SEQ ID NO: 7. Alternatively, the antibody or antigen binding portion thereof binds to at least a portion of an amino acid sequence of SEQ ID NO: 8. In another embodiment of the present invention, the antibody or antigen binding portion thereof binds to at least a portion of an amino acid sequence of SEQ ID NO:2, or at least a portion of an amino acid sequence selected from the group consisting of SEQ ID NOs: 3-6. In a preferred embodiment of this aspect of the present invention, the antibody or binding portion thereof binds to the portion of SEQ ID NO: 2-8 containing the ankyrin repeat domain sequence, i.e., TTPLH (SEQ ID NO:16).

An antibody of the present invention encompasses any immunoglobulin molecule that specifically binds to a GIT1 ankyrin repeat domain as described above. As used herein, the term "antibody" is meant to include intact immunoglobulins derived from natural sources or from recombinant sources, as well as immunoreactive portions (i.e., antigen binding portions) of intact immunoglobulins. The antibodies of the present invention may exist in a variety of forms including, for example, polyclonal antibodies, monoclonal antibodies, intracellular antibodies ("intrabodies"), antibody fragments (e.g. Fv, Fab and F(ab)2), as well as single chain antibodies (scFv), chimeric antibodies, and humanized antibodies (Ed Harlow and David Lane, USING ANTIBODIES: A LABORATORY MANUAL (Cold Spring Harbor Laboratory Press, 1999); Houston et al., "Protein Engineering of Antibody Binding Sites: Recovery of Specific Activity in an Anti-Digoxin Single-Chain Fv Analogue Produced in *Escherichia coli*," *Proc Natl Acad Sci USA* 85:5879-5883 (1988); Bird et al, "Single-Chain Antigen-Binding Proteins," *Science* 242:423-426 (1988), which are hereby incorporated by reference in their entirety).

Methods for monoclonal and polyclonal antibody production may be carried out using the techniques described herein or other well-known in the art (MONOCLONAL ANTIBODIES—PRODUCTION, ENGINEERING AND CLINICAL APPLICATIONS (Mary A. Ritter and Heather M. Ladyman eds., 1995), and Ed Harlow and David Lane, USING ANTIBODIES: A LABORATORY MANUAL (Cold Spring Harbor Laboratory Press, 1988), which are hereby incorporated by reference in its entirety).

For monoclonal antibody production, the process generally involves obtaining immune cells (lymphocytes) from the spleen of a mammal which has been previously immunized with the antigen of interest (i.e., a GIT1 peptide comprising the ankyrin repeat domain, e.g. SEQ ID NOs: 2-8 or any portion thereof as described supra) either in vivo or in vitro. The antibody-secreting lymphocytes are fused with myeloma cells or transformed cells, which are capable of replicating indefinitely in cell culture, thereby producing an immortal, immunoglobulin-secreting cell line. Fusion with mammalian myeloma cells or other fusion partners capable of replicating indefinitely in cell culture is achieved by standard and well-known techniques, for example, by using polyethylene glycol (PEG) or other fusing agents (Milstein and Kohler, "Derivation of Specific Antibody-Producing Tissue Culture and Tumor Lines by Cell Fusion," *Eur J Immunol* 6:511 (1976), which is hereby incorporated by reference in its entirety). The immortal cell line, which may be murine, but may also be derived from cells of other mammalian species, is selected to be deficient in enzymes necessary for the utilization of certain nutrients, to be capable of rapid growth, and have good fusion capability. The resulting fused cells, or hybridomas, are cultured, and the resulting colonies screened for the production of the desired monoclonal antibodies. Colonies producing such antibodies are cloned, and grown either in vivo or in vitro to produce large quantities of antibody.

Alternatively monoclonal antibodies can be made using recombinant DNA methods (i.e. synthetic antibodies) as described in U.S. Pat. No. 4,816,567 to Cabilly et al, which is hereby incorporated by reference in its entirety. The polynucleotide(s) encoding a monoclonal antibody can further be modified using recombinant DNA technology to generate alternative antibodies. For example, the constant domains of the light and heavy chains of a mouse monoclonal antibody can be substituted for those regions of a human antibody to generate a chimeric antibody. Alternatively, the constant domains of the light and heavy chains of a mouse monoclonal antibody can be substituted for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity and affinity of a monoclonal antibody.

The monoclonal antibody of the present invention can be a humanized antibody. Humanized antibodies are antibodies that contain minimal sequences from non-human (e.g., murine) antibodies within the variable regions. Such antibodies are used therapeutically to reduce antigenicity and human anti-mouse antibody responses when administered to a human subject. In practice, humanized antibodies are typically human antibodies with minimal to no non-human sequences. An antibody can be humanized by substituting the complementarity determining region (CDR) of a human antibody with that of a non-human antibody (e.g., mouse, rat, rabbit, hamster, etc.) having the desired specificity, affinity, and capability (Jones et al., "Replacing the Complementarity-Determining Regions in a Human Antibody With Those From a Mouse," *Nature* 321:522-525 (1986); Riechmann et al., "Reshaping Human Antibodies for Therapy," *Nature* 332:323-327 (1988); Verhoeyen et al., "Reshaping Human Antibodies: Grafting an Antilysozyme Activity," *Science* 239:1534-1536 (1988), which are hereby incorporated by reference in their entirety). The humanized antibody can be further modified by the substitution of additional residues either in the Fv framework region and/or within the replaced non-human residues to refine and optimize antibody specificity, affinity, and/or capability.

The GIT1 antibody of the present invention can also be a human monoclonal antibody. A human antibody is an antibody produced by a human or an antibody having an amino acid sequence corresponding to an antibody produced by a human. Human antibodies can be produced using various techniques known in the art. Immortalized human B lymphocytes immunized in vitro or isolated from an immunized individual that produce an antibody directed against a target antigen can be generated (See e.g., Reisfeld et al., MONOCLONAL ANTIBODIES AND CANCER THERAPY 77 (Alan R. Liss ed., 1985) and U.S. Pat. No. 5,750,373 to Garrard, which are hereby incorporated by reference in their entirety). Also, the human antibody can be selected from a phage library, where that phage library expresses human antibodies (Vaughan et al., "Human Antibodies with Sub-Nanomolar Affinities Isolated from a Large Non-immunized Phage Display Library," *Nature Biotechnology,* 14:309-314 (1996); Sheets et al., "Efficient Construction of a Large Nonimmune Phage Antibody Library: The Production of High-Affinity Human Single-Chain Antibodies to Protein Antigens," *Proc. Natl. Acad. Sci. U.S.A.* 95:6157-6162 (1998); Hoogenboom et al., "By-passing Immunisation. Human Antibodies From Synthetic Repertoires of Germline VH Gene Segments Rearranged In Vitro," *J Mol Biol* 227:381-8 (1992); Marks et al., "By-passing Immunization. Human Antibodies from V-gene Libraries Displayed on Phage," *J Mol Biol* 222:581-97 (1991), which are hereby incorporated by reference in their entirety). Human antibodies can also be made in transgenic mice containing human immunoglobulin loci that are capable upon immunization of producing the full repertoire of human antibodies in the absence of endogenous immunoglobulin production. This approach is described in U.S. Pat. No. 5,545,807 to Surani et al.; U.S. Pat. No. 5,545,806 to Lonberg et al.; U.S. Pat. No. 5,569,825 to Lonberg et al.; U.S. Pat. No. 5,625,126 to Lonberg et al.; U.S. Pat. No. 5,633,425 to Lonberg et al.; and U.S. Pat. No. 5,661,016 to Lonberg et al., which are hereby incorporated by reference in their entirety.

Also suitable for use in the present invention are antibody fragments engineered to bind to intracellular proteins, i.e. intrabodies. Intrabodies are generally obtained by selecting a single variable domain from variable regions of an antibody having two variable domains (i.e., a heterodimer of a heavy chain variable domain and a light chain variable domain). Single chain Fv fragments, Fab fragments, ScFv-Cκ fusion proteins, single chain diabodies, $V_H$-$C_H$1 fragments, and even whole IgG molecules are suitable formats for intrabody development (Kontermann R. E., "Intrabodies as Therapeutic Agents," *Methods* 34:163-70 (2004), which is here by incorporated by reference in its entirety).

Intrabodies having antigen specificity for a specific epitope can be obtained from phage display, yeast surface display, or ribosome surface display. Methods for producing libraries of intrabodies and isolating intrabodies of interest are further described in U.S. Published Patent Application No. 20030104402 to Zauderer and U.S. Published Patent Application No. 20050276800 to Rabbitts, which are hereby incorporated by reference in their entirety. Methods for improving the stability and affinity binding characteristics of intrabodies are described in WO2008070363 to Zhenping, and Contreras-Martinez et al., "Intracellular Ribosome Display via SccM Translation Arrest as a Selection for Antibodies with Enhanced Cytosolic Stability," *J Mol Biol* 372(2):513-24 (2007), which are hereby incorporated by reference in their entirety.

Other GIT1 inhibitors that are suitable for use in accordance with this aspect of the present invention include inhibitory GIT1 nucleic acid molecules that interfere with GIT1 expression to cause a reduction in GIT1 expression levels and, hence, overall levels of GIT1 activity. Suitable GIT1 inhibitory nucleic acid molecules include, without limitation, GIT1 siRNA, a GIT1 microRNA, antisense GIT1 RNA, and a GIT1 shRNA.

The use of antisense methods to inhibit the in vivo translation of genes and subsequent protein expression is well known in the art (e.g., U.S. Pat. No. 7,425,544 to Dobie et al.; U.S. Pat. No. 7,307,069 to Karras et al.; U.S. Pat. No. 7,288,530 to Bennett et al.; U.S. Pat. No. 7,179,796 to Cowsert et al., which are hereby incorporated by reference in their entirety). Antisense nucleic acids are nucleic acid molecules (e.g., molecules containing DNA nucleotides, RNA nucleotides, or modifications (e.g., modification that increase the stability of the molecule, such as 2'-O-alkyl (e.g., methyl) substituted nucleotides) or combinations thereof) that are complementary to, or that hybridize to, at least a portion of a specific nucleic acid molecule, such as an mRNA molecule (see e.g., Weintraub, H. M., "Antisense DNA and RNA," *Scientific Am.* 262:40-46 (1990), which is hereby incorporated by reference in its entirety). The antisense nucleic acid molecule hybridizes to its corresponding target nucleic acid molecule, such as the GIT1 mRNA, to form a double-stranded molecule, which interferes with translation of the mRNA, as the cell will not translate a double-stranded mRNA. Antisense nucleic acids used in the methods of the present invention are typically at least 10-12 nucleotides in length, for example, at least 15, 20, 25, 50, 75, or 100 nucleotides in length. The antisense nucleic acid can also be as long as the target nucleic acid with which it is intended to form an inhibitory duplex. Antisense nucleic acids can be introduced into cells as antisense oligonucleotides, or can be produced in a cell in which a nucleic acid encoding the antisense nucleic acid has been introduced, for example, using gene therapy methods.

siRNAs are double stranded synthetic RNA molecules approximately 20-25 nucleotides in length with short 2-3 nucleotide 3' overhangs on both ends. The double stranded siRNA molecule represents the sense and anti-sense strand of a portion of the target mRNA molecule, in this case a portion of the GIT1 nucleotide sequence. The mRNA sequence of GIT1 is known in the art (see NCBI sequence reference numbers NM_001085454 (transcript for GIT1 isoform 1), NM_014030.3 (transcript GIT1 isoform 2), which are hereby incorporated by reference in their entirety). siRNA molecules are typically designed to target a region of the mRNA target approximately 50-100 nucleotides downstream from the start codon. Upon introduction into a cell, the siRNA complex triggers the endogenous RNA interference (RNAi) pathway, resulting in the cleavage and degradation of the target mRNA molecule. siRNA molecules that effectively interfere with GIT1 expression are described herein in the Examples. Various improvements of siRNA compositions, such as the incorporation of modified nucleosides or motifs into one or both strands of the siRNA molecule to enhance stability, specificity, and efficacy, have been described and are suitable for use in accordance with this aspect of the invention (see e.g., WO2004/015107 to Giese et al.; WO2003/070918 to McSwiggen et al.; WO1998/39352 to Imanishi et al.; U.S. Patent Application Publication No. 2002/0068708 to Jesper et al.; U.S. Patent Application Publication No. 2002/0147332 to Kaneko et al; U.S. Patent Application Publication No. 2008/0119427 to Bhat et al., which are hereby incorporated by reference in their entirety). An siRNA specific to GIT1 is described in Example 4.

MicroRNAs (miRNAs) are derived from endogenous genes that are initially transcribed as longer RNA transcripts. In mammals, the primary miRNA transcripts (pri-miRNAs) are processed by the nuclease Drosha into about 70 nt precursor miRNAs (pre-miRNAs) that are exported by exportin-5 to the cytoplasm. The Dicer nuclease excises the mature miRNAs from pre-miRNAs. miRNAs are bound to proteins that belong to the Argonaute family and, in humans, may also assemble with other proteins, including the Gemin3 and Gemin4 proteins, to form micro-Ribonucleoprotein complexes (miRNPs). Many miRNAs, like siRNAs, function by base pairing with miRNA-recognition elements (MREs) found in their mRNA targets and direct either target RNA endonucleolytic cleavage or translational repression. The manner by which a miRNA or siRNA base pairs with its mRNA target correlates with its function. If the complementarity between a miRNA and its target is extensive, the RNA target is cleaved, if the complementarity is partial, the stability of the target mRNA in not affected but its translation is repressed.

Short or small hairpin RNA molecules are similar to siRNA molecules in function, but comprise longer RNA sequences that make a tight hairpin turn. shRNA is cleaved by cellular machinery into siRNA and gene expression is silenced via the cellular RNA interference pathway. shRNA molecules that effectively silence GIT1 expression are known in the art and are commercially available (OriGene, Rockville, Md.).

Another aspect of the present invention relates to an isolated GIT1 peptide comprising the ankyrin repeat domain as described supra. Specifically, isolated peptides of the present invention may comprise the amino acid sequence of SEQ ID NO: 7, SEQ ID NO: 8, or an RBP-J binding fragment thereof. Suitable smaller peptides derived from SEQ ID NOs: 7 or 8, include peptides comprising residues 1-30 of SEQ ID NOs: 7 or 8 corresponding to the first ANK domain, residues 35-64 of SEQ ID NOs: 7 or 8 corresponding to the second ANK domain, residues 36-48 of SEQ ID NOs: 7 or 8 corresponding to a core region with the second ANK domain, and residues 68-97 of SEQ ID NOs: 7 or 8 corresponding to the third ANK domain. In another embodiment of the present invention, the isolated peptide of the present invention may comprise the amino acid sequence of the human ANK domain, i.e., residues 132-228 of SEQ ID NO: 1 (also shown above as SEQ ID NO: 2) or fragments thereof. Suitable smaller peptides derived from the human ANK domain, include peptides comprising residues 132-161 of SEQ ID NO: 1 or residues 1-30 of SEQ ID NO:2 corresponding to the first ANK domain (i.e., DLSKQLHSS-VRTGNLETCLRLLSLGAQANF), residues 166-195 of SEQ ID NO: 1 or residues 35-64 of SEQ ID NO:2 corresponding to the second ANK domain (i.e., KGTTPL-HVAAKAGQTLQAELLVVYGADPGS), residues 167-179 of SEQ ID NO: 1 or residues 36-48 of SEQ ID NO: 2 corresponding to a core region with the second ANK domain (i.e., GTTPLHVAAKAGQ), and residues 199-228 of SEQ ID NO: 1 or residues 68-97 of SEQ ID NO: 2 corresponding to the third ANK domain (i.e., NGRTPIDYARQAGHHE-LAERLVECQYELTD). In another embodiment of the present invention, the isolated GIT1 peptide of the present invention comprises an amino acid sequence selected from the amino acid sequences of SEQ ID NOs: 3-6, or smaller fragments thereof.

Another aspect of the present invention relates to an isolated nucleic acid molecule encoding a GIT1 peptide of the present invention. An exemplary isolated nucleic acid molecule encoding the amino acid sequence of SEQ ID NO: 2 comprises a nucleotide sequence of SEQ ID NO: 9 as shown below.

```
                                            (SEQ ID NO: 9)
AAA GAT CTG AGC AAA CAG CTG CAT AGC AGC GTG CGC

ACC GGC AAC CTG GAA ACC TGC CTG CGC CTG CTG AGC

CTG GGC GCG CAG GCG AAC TTT TTT CAT CCG GAA AAA

GGC ACC ACC CCG CTG CAT GTG GCG GCG AAA GCG GGC

CAG ACC CTG CAG GCG GAA CTG CTG GTG GTG TAT GGC
```

Due to the degeneracy of the DNA code, one of skill in the art readily appreciates that other nucleotide sequences will also encode an amino acid sequence of SEQ ID NO:2, or encode the functional equivalent of SEQ ID NO:2 (e.g., any one of SEQ ID NOs: 3-6). Additional GIT1 nucleic acid molecules can be identified based upon their alignment with the GIT1 nucleotide sequence of SEQ ID NO: 9 provided above, where such alignment preferably is at least about 60 percent identical, more preferably at least about 70 percent, 75 percent, 80 percent, 85 percent, 90 percent, or 95 percent identical. Accordingly, another exemplary isolated nucleic acid molecule encoding the amino acid sequence of SEQ ID NO: 2 comprises the nucleotide sequence of SEQ ID NO: 10 as shown below.

```
                                           (SEQ ID NO: 10)
AAR GAY YTN WSN AAR CAR YTN CAY WSN WSN GTN MGN

CAN GGN AAY YTN GAR CAN TGY YTN MGN YTN YTN WSN

YTN GGN GCN CAR GCN AAY TTY TTY CAY CCN GAR AAR

GGN CAN CAN CCN YTN CAY GTN GCN GCN AAR GCN GGN

CAR CAN YTN CAR GCN GAR YTN YTN GTN GTN TAY GGN
```

The variable residues within SEQ ID NO: 10 are defined as follows: R is A or G; Y is T or C; N is G, A, T or C; W is A or T; and M is A or C.

The nucleic acids may be present in whole cells, in a cell lysate, or in a partially purified or substantially pure form (i.e., purified away from other cellular components or other contaminants).

The peptides of the present invention can be synthesized by solid phase or solution phase peptide synthesis, recombinant expression, or can be obtained from natural sources. Automatic peptide synthesizers are commercially available from numerous suppliers, such as Applied Biosystems, Foster City, Calif. Standard techniques of chemical peptide synthesis are well known in the art (see e.g., SYNTHETIC PEPTIDES: A USERS GUIDE 93-210 (Gregory A. Grant ed., 1992), which is hereby incorporated by reference in its entirety). Alternatively, peptides of the present invention can be produced via recombinant expression systems as described in more detail below.

Generally, the use of recombinant expression systems involves inserting the nucleic acid molecule encoding the amino acid sequence of the desired GIT1 peptide into an expression system to which the molecule is heterologous (i.e., not normally present). Suitable nucleic acid molecules encoding the peptides of the present invention are provided above as SEQ ID NO: 9 and SEQ ID NO: 10.

One or more desired nucleic acid molecules encoding a peptide of the invention may be inserted into the vector. When multiple nucleic acid molecules are inserted, the multiple nucleic acid molecules may encode the same or different peptides. The heterologous nucleic acid molecule is inserted into the expression system or vector in proper sense (5'→3') orientation relative to the promoter and any other 5' regulatory molecules, and correct reading frame.

The preparation of the nucleic acid constructs can be carried out using standard cloning procedures well known in the art as described by Joseph Sambrook et al., MOLECULAR CLONING: A LABORATORY MANUAL (Cold Springs Harbor 1989). U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in a suitable host cell.

A variety of genetic signals and processing events that control many levels of gene expression (e.g., DNA transcription and messenger RNA ("mRNA") translation) can be incorporated into the nucleic acid construct to maximize peptide production. For the purposes of expressing a cloned nucleic acid sequence encoding a desired peptide, it is advantageous to use strong promoters to obtain a high level of transcription. Depending upon the host system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited to, lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene. Common promoters suitable for directing expression in mammalian cells include, without limitation, SV40, MMTV, metallothionein-1, adenovirus E1a, CMV, immediate early, immunoglobulin heavy chain promoter and enhancer, and RSV-LTR.

A nucleic acid molecule encoding an isolated peptide of the present invention, a promoter molecule of choice, including, without limitation, enhancers, and leader sequences; a suitable 3' regulatory region to allow transcription in the host, and any additional desired components, such as reporter or marker genes, are cloned into the vector of choice using standard cloning procedures in the art, such as described in Joseph Sambrook et al., MOLECULAR CLONING: A LABORATORY MANUAL (Cold Springs Harbor 1989); Frederick M. Ausubel, SHORT PROTOCOLS IN MOLECULAR BIOLOGY (Wiley 1999), Roberts and Lauer, "Maximizing Gene Expression On a Plasmid Using Recombination In Vitro," *Methods in Enzymology* 68:473-82 (1979), and U.S. Pat. No. 4,237,224 to Cohen and Boyer, which are hereby incorporated by reference in their entirety. Once the nucleic acid molecule encoding the peptide has been cloned into an expression vector, it is incorporated into a host. Recombinant molecules can be introduced into cells, without limitation, via transfection (if the host is a eukaryote), transduction, conjugation, mobilization, or electroporation, lipofection, protoplast fusion, mobilization, or particle bombardment, using standard cloning procedures known in the art, as described by JOSEPH SAMBROOK et al., MOLECULAR CLONING: A LABORATORY MANUAL (Cold Springs Harbor 1989), which is hereby incorporated by reference in its entirety.

A variety of suitable host-vector systems may be utilized to express the recombinant GIT1 peptide of the present invention. Primarily, the vector system must be compatible with the host used. Host-vector systems include, without limitation, the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria.

Recombinantly expressed peptides can be purified using any one of several methods readily known in the art, including ion exchange chromatography, hydrophobic interaction chromatography, affinity chromatography, gel filtration, and reverse phase chromatography. The peptide is preferably produced in purified form (preferably at least about 80% or 85% pure, more preferably at least about 90% or 95% pure) by conventional techniques. Depending on whether the recombinant host cell is made to secrete the peptide into growth medium (see U.S. Pat. No. 6,596,509 to Bauer et al., which is hereby incorporated by reference in its entirety), the peptide can be isolated and purified by centrifugation (to separate cellular components from supernatant containing the secreted peptide) followed by sequential ammonium sulfate precipitation of the supernatant. The fraction containing the peptide is subjected to gel filtration in an appropriately sized dextran or polyacrylamide column to separate the peptides from other proteins. If necessary, the peptide fraction may be further purified by HPLC.

The GIT1 peptides of the present invention can be coupled to one or more targeting moieties. A targeting moiety according to the present invention functions to (i) target the GIT1 peptide to a particular cell or tissue type (e.g., signaling peptide sequence) upon administration to a subject in accordance with the methods of the present invention and/or (ii) to promote the cellular uptake of the GIT1 peptide after administration to a subject.

To achieve cell-specific delivery of the GIT1 ANK peptide or other GIT1 inhibitory peptides, the peptide is coupled to a cell-specific targeting moiety. A cell-specific targeting moiety confers cell-type specific binding to the peptide, and it is chosen on the basis of the particular cell population to be targeted. The cell-specific targeting moiety can be any type of moiety, such as an antibody, a growth factor, a hormone, a polypeptide, a peptide, an aptamer, or a cytokine that binds to a corresponding binding partner present on the surface of the target cell. In particular embodiments, the cell-specific targeting moiety is an antibody. For example, the antibody may be a full-length antibody, chimeric antibody, Fab', Fab, F(ab')$_2$, single domain antibody (DAB), Fv, single chain Fv (scFv), minibody, diabody, triabody, or a mixture thereof.

In one embodiment of the present invention, the cell specific targeting moiety is an endothelial cell targeting moiety. A number of endothelial cell specific targeting moieties are known in the art and are suitable for use in accordance with the methods and compositions of the present invention. One exemplary endothelial cell targeting moiety comprises an Arg-Gly-Asp (RGD) tripeptide sequence motif that has specific binding affinity for the $\alpha_5\beta_3$ integrin abundantly present on the endothelial cell surface (Curnis et al., *Cancer Research* 64(2): 565-571 (2004), which is hereby incorporated by reference in its entirety). Another $\alpha_5\beta_3$ integrin specific peptide sequence useful for endothelial cell targeting comprises PHSRN (SEQ ID NO: 11).

Another exemplary endothelial cell targeting moiety useful for targeting the GIT1 peptide of the present invention to endothelial cells comprises an Asn-Gly-Arg (NGR) tripeptide sequence motif. The NGR tripeptide sequence is a ligand for aminopeptidase N isoform CD13 that is abundantly expressed on endothelial cells. Other endothelial cell targeting moiety sequences that are suitable for use in the methods and compositions of the present invention include YIGSR (SEQ ID NO: 12), and HWGF (SEQ ID NO: 13) (Turunen et al., "Peptide-Retargeted Adenovirus Encoding a Tissue Inhibitor of Metalloproteinase-1 Decreases Restenosis after Intravascular Gene Transfer," *Mol Ther.* 6(3):306-12 (2002); Jun et al., "Endothelialization of Microporous YIGSR/PEG-modified Polyurethaneurea," *Tissue Engineering* 11(7-8):1133-1140 (2005), which are hereby incorporated by reference in their entirety).

In an alternative embodiment of the invention, the endothelial cell targeting moiety comprises an endothelial cell surface receptor ligand having binding specificity for an endothelial cell surface receptor. Non-limiting examples of endothelial cell surface receptor ligands that can be utilized as endothelial cell targeting moieties in the present invention include, without limitation, VEGF (including VEGF isoforms $VEGF_{121}$, $VEGF_{165}$, $VEGF_{189}$, $VEGF_{206}$), FGF, integrin, fibronectin, ICAM, PDGF, P-selectin ligand, VCAM-1 ligand, ICAM-1 ligand. In another embodiment of the present invention, the endothelial cell surface moiety comprises an antibody that binds to an endothelial cell surface protein. Exemplary antibodies include, without limitation, anti-VEGFR1 antibody, anti-VCAM1 antibody, anti-ICAM-1 antibody, anti-P-selectin antibody, and anti-aminopeptidase N antibody.

In another embodiment of the present invention, the GIT1 peptide is coupled to a "cell-penetrating moiety" to promote cellular uptake of the GIT1 peptide upon delivery to the target cell, e.g. target endothelial cell. Suitable cell penetrating moieties include cell penetrating peptides (CPP) that translocate across the plasma membrane of eukaryotic cells by a seemingly energy-independent pathway. CPPs have been used successfully for intracellular delivery of macromolecules, including antibodies, peptides, proteins, and nucleic acids, with molecular weights several times greater than their own. Many cell-penetrating peptides are designed from sequences of membrane-interacting proteins such as fusion proteins, signal peptides, transmembrane domains and antimicrobial peptides (Morris et al., "Translocating peptides and proteins and their use for gene delivery" *CURR OPIN BIOTECHNOL* 5:461-466 (2000); Jarver et al., "The Use of Cell-Penetrating Peptides as a Tool for Gene Regulation" *Drug Discov Today* 9:395-402 (2004); El-Andaloussi et al., "Cell-Penetrating Peptides: Mechanisms and Applications" *Curr Pharm Des* 28:3597-3611 (2005), each of which is hereby incorporated by reference in its entirety. Within these sequences, short sequences called Protein Transduction Domains (PTDs) efficiently cross biological membranes without the need of a carrier or of a receptor to deliver peptides or proteins into intracellular compartments. Several commonly used cell penetrating moieties include, without limitation, the third helix of the homeodomain of antennapedia called penetratin, the Tat peptide derived from the transactivating protein Tat of HIV-1 (amino acids 49-57 of HIV Tat protein), transportan and VP22.

A second category of cell-penetrating peptides, designated as amphipathic peptides, are also suitable for use in the present invention. An amphipathic molecule can be defined, in short, as consisting of two domains: a hydrophilic (polar) domain and a hydrophobic (non-polar) domain. For peptides, the amphipathic character can arise either from the primary structure, or from the secondary structure. Primary amphipathic peptides can be defined as the sequential assembly of a domain of hydrophobic residues with a domain of hydrophilic residues. Secondary amphipathic peptides are generated by the conformational state which allows the positioning of the hydrophobic and hydrophilic residues on opposite sides of the molecule.

Other peptides, such as polyarginine-based peptides, calcitonin-derived peptides, and oligomers, are also suitable cell penetrating peptides that can be coupled to the GIT1 peptides of the present invention to achieve intracellular peptide delivery.

In some embodiments of the present invention, the isolated GIT1 peptide of the present invention is coupled to a tag. A "tag" as used herein includes any labeling moiety that facilitates the detection, quantitation, separation, and/or purification of the isolated GIT1 peptide of the present invention. Suitable tags include purification tags, and radioactive, enzymatic, or fluorescent detectable labels. Any detectable label recognized in the art as being useful in various assays could be used in the present invention. In particular, the detectable label component can include compositions detectable by spectroscopic, photochemical, biochemical, immunochemical, or chemical means. As such, the label component produces a detectable signal. For instance, suitable labels include soluble dyes, fluorescent dyes, chemiluminescent compounds, radioisotopes, electron-dense reagents, enzymes, colored particles, or dioxigenin. The label component can generate a measurable signal, such as radioactivity, fluorescent light, color, or enzyme activity, which can be used to identify and quantify the amount of label bound to a capture site. Thus, the label component can also represent the presence or absence of a particular antigen bound thereto.

The GIT1 peptides of the present invention can be coupled to the one or more targeting moieties or tags by way of a short linker sequence. Suitable linker sequences include glycine (e.g. $G_{3-5}$) or serine-rich (e.g. GSG, GSGS (SEQ ID NO: 14), GSGSG (SEQ ID NO: 15), $GS_NG$) linker sequences. Alternatively, the targeting moiety or tag can be coupled to the isolated peptide of the present invention by chemical coupling in any suitable manner known in the art. In one embodiment, the chemical cross-linking method is a non-specific method, i.e. the point of coupling is not directed to any particular site on the transport or cargo peptide or polypeptide. Alternatively, the targeting moiety can be directly coupled to the isolated peptide of the present invention via a functional group (e.g., cysteine residue or primary amine), found only once or a few times in one or both of the targeting moiety and cargo peptide to be cross-linked.

Coupling of the two constituents can be accomplished via a coupling or conjugating agent. There are several intermolecular cross-linking reagents which can be utilized, e.g., J-succinimidyl 3-(2-pyridyldithio)propionate (SPDP) or N,N'-(1,3-phenylene)bismaleimide (both of which are highly specific for sulfhydryl groups and form irreversible linkages); N,N'-ethylene-bis-(iodoacetamide) or other such reagent having 6 to 11 carbon methylene bridges (which are relatively specific for sulfhydryl groups); and 1,5-difluoro-2,4-dinitrobenzene (which forms irreversible linkages with amino and tyrosine groups). Other cross-linking reagents useful for this purpose include, without limitation, p,p'-difluoro-m,m'-dinitrodiphenylsulfone (which forms irreversible cross-linkages with amino and phenolic groups); dimethyl adipimidate (which is specific for amino groups); phenol-1,4-disulfonylchloride (which reacts principally with amino groups); hexamethylenediisocyanate or diisothiocyanate, or azophenyl-p-diisocyanate (which reacts principally with amino groups); glutaraldehyde (which reacts with several different side chains) and disdiazobenzidine (which reacts primarily with tyrosine and histidine). Heterobifunctional cross-linking agents having two different functional groups, e.g., amine- and thiol-reactive groups, that will cross-link two proteins having free amines and thiols, respectively, are also suitable cross-linking agents.

Examples of heterobifunctional cross-linking agents include succinimidyl 4-(N-maleimidomethyl)cyclohexane-1-carboxylate, m-maleimidobenzoyl-N-hydroxysuccinimide ester, and succinimide 4-(p-maleimidophenyl)butyrate. The succinimidyl group of these cross-linkers reacts with a primary amine, and the thiol-reactive maleimide forms a covalent bond with the thiol of a cysteine residue.

In one embodiment of the present invention, a cross-linking reagent that forms a cleavable covalent bond (e.g., disulfide bond) under cellular conditions is preferentially utilized. Exemplary cross-linking agents that form cleavable bonds include, without limitation, Traut's reagent, dithiobis (succinimidylpropionate), and N-succinimidyl 3-(2-pyridyldithio)propionate. The use of a cleavable cross-linking reagent permits the cargo moiety (i.e., the GIT1 peptide) to separate from the targeting moiety after delivery into the target cell.

Another aspect of the present invention is directed to pharmaceutical compositions comprising any one of the therapeutic GIT1 agents described herein.

In one embodiment of this aspect of the invention, the pharmaceutical agent comprises a GIT1 inhibitory peptide comprising an ankryin repeat domain (e.g., a peptide comprising an amino acid sequence of SEQ ID NOs: 2-8, of fragments thereof as described supra) or the SHD domain (e.g., a peptide comprising an amino acid sequence of SEQ ID Nos: 17 or 18), and a pharmaceutically acceptable carrier. In another embodiment of this aspect of the invention, the pharmaceutical agent comprises a GIT1 antibody or GIT1 inhibitory nucleic acid, and a pharmaceutically acceptable carrier.

The pharmaceutical composition of the present invention can further contain, in addition to the GIT1 therapeutic component, other pharmaceutically acceptable components (see REMINGTON'S PHARMACEUTICAL SCIENCE (19th ed., 1995), which is hereby incorporated by reference in its entirety). The incorporation of such pharmaceutically acceptable components depends on the intended mode of administration and therapeutic application of the pharmaceutical composition. Typically, however, the pharmaceutical composition will include a pharmaceutically-acceptable, non-toxic carrier or diluent, which are defined as vehicles commonly used to formulate pharmaceutical compositions for animal or human administration. The diluent is selected so as not to affect the biological activity of the composition. Exemplary carriers or diluents include distilled water, physiological phosphate-buffered saline, Ringer's solutions, dextrose solution, and Hank's solution.

Pharmaceutical compositions can also include large, slowly metabolized macromolecules such as proteins, polysaccharides such as chitosan, polylactic acids, polyglycolic acids and copolymers (such as latex functionalized sepharose, agarose, cellulose), polymeric amino acids, amino acid copolymers, and lipid aggregates (such as oil droplets or liposomes).

In some embodiments of the present invention, the pharmaceutical composition or therapeutic agents themselves (i.e., GIT1 peptides) are housed in a delivery vehicle. Any suitable passive or targeted delivery vehicle can be employed including, but not limited to, viral vectors, biodegradable microspheres, microparticles, nanoparticles, liposomes, collagen minipellets, and cochleates.

In one embodiment of the present invention, the delivery vehicle is a liposome delivery vehicle. Liposomes are vesicles comprised of one or more concentrically ordered lipid bilayers which encapsulate an aqueous phase. A liposome which includes a GIT1 inhibitor (e.g., GIT1 peptide or nucleic acid inhibitor) is contacted with the target cell under conditions effective for delivery of the therapeutic into the target cell, e.g., an endothelial cell. For direct administration, the liposomal vesicles need not be targeted to endothelial cells per se. Alternatively, the liposome delivery system can be made to accumulate at a target organ, tissue, or cell via active targeting (e.g., by incorporating an antibody or other ligand on the surface of the liposomal vehicle). This can be achieved using any of the endothelial cell targeting moieties described supra. See also, Holig et al., "Novel RGD Lipopeptides for Targeting of Liposomes to Integrin-Expressing Endothelial and Melanoma Cells," *Protein Engineering Design Selection* 17(5):433-441 (2004) and Vader et al., "Targeted Delivery of Small Interfering RNA to Angiogenic Endothelial Cells with Liposome-Polycation-DNA Particles," *J. Control Release* 160(2):211-6 (2011), which are hereby incorporated by reference in their entirety.

Different types of liposomes can be prepared according to Bangham et al., "Diffusion of Univalent Ions across the Lamellae of Swollen Phospholipids," *J. Mol. Biol.* 13:238-252 (1965); U.S. Pat. No. 5,653,996 to Hsu et al.; U.S. Pat. No. 5,643,599 to Lee et al.; U.S. Pat. No. 5,885,613 to Holland et al.; U.S. Pat. No. 5,631,237 to Dzau et al.; and U.S. Pat. No. 5,059,421 to Loughrey et al., each of which is hereby incorporated by reference in its entirety.

These liposomes can be produced such that they contain, in addition to the GIT1 therapeutic agents, other therapeutic agents, such as other anti-angiogenic agents, which would also be released at the target site.

In another embodiment of the present invention, the delivery vehicle is a nanoparticle. A variety of nanoparticle delivery vehicles are known in the art and are suitable for delivery of a GIT1 therapeutic agent of the invention. A nanoparticle delivery system can be made to accumulate at a target organ, tissue, or cell via active targeting (e.g., by incorporating an antibody or other ligand on the surface of the nanoparticle vehicle) (see e.g., Oda et al., "Nanoparticle-Mediated Endothelial Cell-Selective Delivery of Pitavastatin Induces Functional Collateral Arteries (Therapeutic Arteriogenesis) in a Rabbit Model of Chronic Hind Limb Ischemia," *J. Vasc. Surg.* 52(2):412-420 (2010), which is hereby incorporated by reference in its entirety). Any of the endothelial cell targeting moieties described supra can be coupled to the nanoparticle delivery vehicle to achieve cell specific delivery.

Suitable nanoparticles include conjugated pH-sensitive lipopolyplex nanoparticles (LPs) as described by Jin et al., "Targeted Delivery of Antisense Oligodeoxynucleotide by Transferrin Conjugated pH-sensitive Lipopolyplex Nanoparticles: A Novel Oligonucleotide-based Therapeutic Strategy in Acute Myeloid Leukemia," *Mol. Pharm.* 7(1):196-206 (2010), which is hereby incorporated by reference in its entirety. The lipopolyplex nanoparticle carrying a therapeutic agent (e.g. GIT1 peptide) releases its cargo at acidic endosomal pH to facilitate the cytoplasmic delivery of the therapeutic agent after endocytosis. Other suitable nanoparticles include, without limitation, poly(beta-amino esters) (Sawicki et al., "Nanoparticle Delivery of Suicide DNA for Epithelial Ovarian Cancer Cell Therapy," *Adv. Exp. Med. Biol.* 622:209-219 (2008), which is hereby incorporated by reference in its entirety), polyethylenimine-alt-poly(ethylene glycol) copolymers (Park et al., "Degradable Polyethylenimine-alt-Poly(ethylene glycol) Copolymers As Novel Gene Carriers," *J. Control Release* 105(3):367-80 (2005) and Park et al., "Intratumoral Administration of Anti-KITENIN shRNA-Loaded PEI-alt-PEG Nanoparticles Suppressed Colon Carcinoma Established Subcutaneously in Mice," *J Nanosci. Nanotechnology* 10(5):3280-3 (2010), which are hereby incorporated by reference in their entirety), and liposome-entrapped siRNA nanoparticles (Kenny et al., "Novel Multifunctional Nanoparticle Mediates siRNA Tumor Delivery, Visualization and Therapeutic Tumor Reduction In Vivo," *J. Control Release* 149(2): 111-116 (2011), which is hereby incorporated by reference in its entirety). Nanoparticles may also be formed from compatible polymers and biomaterials such as poly(lactide-co-glycolide) (PLGA), poly(lactide) (PLA), poly(epsilon-caprolactone), albumin, and chitosan. Other nanoparticle delivery vehicles suitable for use in the present invention include microcapsule nanotube devices disclosed in U.S. Patent Publication No. 2010/0215724 to Prakash et al., which is hereby incorporated by reference in its entirety.

In another embodiment of the present invention, the delivery vehicle is a viral vector. Viral vectors are particularly suitable for the delivery of inhibitory nucleic acid molecules, such as GIT1 siRNA or shRNA molecules. Suitable gene therapy vectors include, without limitation, adenoviral vectors, adeno-associated viral vectors, retroviral vectors, lentiviral vectors, and herpes viral vectors.

Adenoviral viral vector delivery vehicles can be readily prepared and utilized as described in Berkner, "Development of Adenovirus Vectors for the Expression of Heterologous Genes," *Biotechniques* 6:616-627 (1988) and Rosenfeld et al., "Adenovirus-Mediated Transfer of a Recombinant Alpha 1-Antitrypsin Gene to the Lung Epithelium In Vivo," *Science* 252:431-434 (1991), WO 93/07283 to Curiel et al., WO 93/06223 to Perricaudet et al., and WO 93/07282 to Curiel et al., which are hereby incorporated by reference in their entirety. Adeno-associated viral delivery vehicles can be constructed and used to deliver an inhibitory nucleic acid molecule of the present invention to cells as described in Shi et al., "Therapeutic Expression of an Anti-Death Receptor-5 Single-Chain Fixed Variable Region Prevents Tumor Growth in Mice," *Cancer Res.* 66:11946-53 (2006); Fukuchi et al., "Anti-Aβ Single-Chain Antibody Delivery via Adeno-Associated Virus for Treatment of Alzheimer's Disease," *Neurobiol. Dis.* 23:502-511 (2006); Chatterjee et al., "Dual-Target Inhibition of HIV-1 In Vitro by Means of an Adeno-Associated Virus Antisense Vector," *Science* 258:1485-1488 (1992); Ponnazhagan et al., "Suppression of Human Alpha-Globin Gene Expression Mediated by the Recombinant Adeno-Associated Virus 2-Based Antisense Vectors," *J. Exp. Med.* 179:733-738 (1994); and Zhou et al., "Adeno-associated Virus 2-Mediated Transduction and Erythroid Cell-Specific Expression of a Human Beta-Globin Gene," *Gene Ther.* 3:223-229 (1996), which are hereby incorporated by reference in their entirety. In vivo use of these vehicles is described in Flotte et al., "Stable in Vivo Expression of the Cystic Fibrosis Transmembrane Conductance Regulator With an Adeno-Associated Virus Vector," *Proc. Nat'l. Acad. Sci.* 90:10613-10617 (1993) and Kaplitt et al., "Long-Term Gene Expression and Phenotypic Correction Using Adeno-Associated Virus Vectors in the Mammalian Brain," *Nature Genet.* 8:148-153 (1994), which are hereby incorporated by reference in their entirety. Additional types of adenovirus vectors are described in U.S. Pat. No. 6,057,155 to Wickham et al.; U.S. Pat. No. 6,033,908 to Bout et al.; U.S. Pat. No. 6,001,557 to Wilson et al.; U.S. Pat. No. 5,994,132 to Chamberlain et al.; U.S. Pat. No. 5,981,225 to Kochanek et al.; U.S. Pat. No. 5,885,808 to Spooner et al.; and U.S. Pat. No. 5,871,727 to Curiel, which are hereby incorporated by reference in their entirety.

Retroviral vectors which have been modified to form infective transformation systems can also be used to deliver a nucleic acid molecule to a target cell. One such type of retroviral vector is disclosed in U.S. Pat. No. 5,849,586 to Kriegler et al., which is hereby incorporated by reference. Other nucleic acid delivery vehicles suitable for use in the present invention include those disclosed in U.S. Patent Publication No. 20070219118 to Lu et al., which is hereby incorporated by reference in its entirety.

Viral vectors are administered to a subject by, for example, intravenous injection, local administration (U.S. Pat. No. 5,328,470 to Nabel et al., which is hereby incorporated by reference in its entirety) or by stereotactic injection (see e.g., Chen et al., "Gene Therapy for Brain Tumors: Regression of Experimental Gliomas by Adenovirus Mediated Gene Transfer In Vivo," *Proc. Nat'l. Acad. Sci. USA* 91:3054-3057 (1994), which is hereby incorporated by reference in its entirety). The pharmaceutical preparation of a viral vector can include the vector in an acceptable diluent, or can comprise a slow release matrix in which the gene delivery vehicle is imbedded.

In practicing the methods of the present invention, the administering step is carried out to achieve a decrease in GIT1 activity. In some embodiments of the present invention such administration is carried out systemically. Alternatively, such administration is carried out via direct or local administration. By way of example, suitable modes of systemic administration include, without limitation, orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes. Suitable modes of local administration include, without limitation, catheterization, implantation, direct injection, dermal/transdermal application, stenting, ear/eye drops, or portal vein administration to relevant tissues, or any other local administration technique, method or procedure, as is generally known in the art.

The therapeutic agents of the present invention may be orally administered, for example, with an inert diluent, or with an assimilable edible carrier, or it may be enclosed in hard or soft shell capsules, or it may be compressed into tablets, or they may be incorporated directly with the food of the diet. Agents of the present invention may also be administered in a time release manner incorporated within such devices as time-release capsules or nanotubes. Such devices afford flexibility relative to time and dosage. For oral therapeutic administration, the agents of the present invention may be incorporated with excipients and used in the form of tablets, capsules, elixirs, suspensions, syrups, and the like. Such compositions and preparations should contain at least 0.1% of the agent, although lower concentrations may be effective and indeed optimal. The percentage of the agent in these compositions may, of course, be varied and may conveniently be between about 2% to about 60% of the weight of the unit. The amount of an agent of the present invention in such therapeutically useful compositions is such that a suitable dosage will be obtained.

When the GIT1 therapeutic agents of the present invention are administered parenterally, solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

Pharmaceutical formulations suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

When it is desirable to deliver the agents of the present invention systemically, they may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Intraperitoneal or intrathecal administration of the agents of the present invention can also be achieved using infusion pump devices. Such devices allow continuous infusion of desired compounds avoiding multiple injections and multiple manipulations.

Compositions containing GIT1 therapeutic agents may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

Effective doses of the compositions of the present invention, for the treatment of conditions associated with abnormal angiogenesis vary depending upon many different factors, including the particular conditions, means of administration, target site, physiological state of the patient, other medications or therapies administered, and physical state of the patient relative to other medical complications. Treatment dosages need to be titrated to optimize safety and efficacy using methods known to those of skill in the art.

EXAMPLES

The following examples are provided to illustrate embodiments of the present invention but they are by no means intended to limit its scope.

Materials and Methods for Examples

Generation of Global and Endothelial Cell (EC)-Specific GIT1 KO.

Global GIT1 KO mice were generated as described before (Pang et al., *Circulation* 1524 (2009), which is hereby incorporated by reference in its entirety). To generate the conditional GIT1 KO mice, exons 3 to 7 of Git1 were targeted by flanking them with loxP sites, in combination with an frt-flanked neomycin phosphotransferase module to positively select putative homologous recombinant ES cells. Correctly targeted recombinants were identified with Xba I and EcoR I restriction digest and Southern blot and PCR by amplifying the region with the primers 5'-TAC AGT GTG GAA ATG GGA AGT GAA AGC-3' (SEQ ID NO: 19) and 5'-GGA GAA GGT GCC AGG AAG GCT TTA-3' (SEQ ID NO: 20), then digesting the products with EcoR I. Only the recombinant fragments will be digested by EcoR I, producing fragments of 347 and 221 bp while the wild-type remains a 521 bp fragment. Following implantation of ES cells into blastocysts, chimeric mice were generated and bred to the F1 generation. Then Git1-targeted mice were bred with Flp transgenic mice to delete the neomycin selection cassette. Progeny were crossed to remove the Flp transgene, resulting in mice bearing floxed Git1 alleles (heterozygous Git1$^{f/+}$; homozygous Git1$^{f/f}$). There are two independently generated floxed Git1 mouse lines. To generate homozygous floxed Git1-Cre recombinase mice, mice carrying both a Tie2-Cre transgene and one floxed Git1 allele were bred to homozygous floxed Git1 mice. The presence of the floxed Git1 gene was detected by PCR. Only homozygous KO animals (ie, GIT1$^{f/f;Tie2-Cre+}$, EC-GIT1 KO) and control littermates (GIT1$^{f/f;Tie2-Cre-}$) were used.

Retina Whole Mount Immunohistochemistry.

Mouse pups were anesthetized by 2% isofluorane and sacrificed at P5. Eyes were fixed in 4% paraformaldehyde (PFA) in PBS at 4° C. overnight and washed in PBS. Retinas were dissected, permeabilized in PBS, 5% Normal goat serum (NGS), and 0.3% Triton X-100 at 4° C. overnight. Then they were rinsed in PBS and incubated in FITC-conjugated isolectin B4 (*Bandeiraea simplicifolia*; L-2140; Sigma-Aldrich) 20 µg/ml in PBS at 4° C. overnight. After washing and a brief post-fixation in PFA, the retinas were either flat mounted or processed for multiple labeling. The following antibodies were used: GIT1 (1:100; Santa Cruz) and Alexa-568 conjugated secondary antibodies (Molecular Probes). Flat mounted retinas were analyzed by fluorescence microscopy using an Olympus BX51 microscope equipped with a digital camera (Spot CCD camera) and by confocal laser scanning microscopy (Olympus confocal system (Fluoroview)). Images were processed using Adobe Photoshop®.

Cell Culture.

Human umbilical vein endothelial cells (HUVECs) were isolated and grown in Medium 200 with low serum growth supplement (Cascade Biologics, Inc., Portland, Oreg.) as described previously (Carmeliet et al., *Nature* 436:193 (2005), which is hereby incorporated by reference in its entirety). GIT1 siRNA (AAGCTGCCAAGAAGAAGC-TAC) (SEQ ID NO: 21) and control non-silencing siRNA (AATTCTCCGACACGTGTCACT) (SEQ ID NO: 22) were designed and synthesized (Ambion) and Dll4 siRNA was purchased (Santa Cruz). The siRNA were transfected at 100 nM for 48 h as previously described by our laboratory (Yin et al., *Mol. Cell Biol.,* 24:875 (2004), which is hereby incorporated by reference in its entirety). HEK293 cells were cultured in Dulbecco's modified Eagle's medium supplemented with 10% fetal bovine serum (FBS), penicillin, and streptomycin at 37° C. in 5% $CO_2$. HEK293T cells were transfected by Lipofectamine/plus (Invitrogen).

Immunoprecipitation and Immunoblotting.

For immunoblotting, cells were lysed in RIPA buffer (150 mM NaCl, 1% Nonidet P-40, 60.5% deoxycholic acid, 0.1% SDS, 50 mM Tris-HCl, pH 8.0). Protein concentrations in the lysates were determined. The protein samples were separated by SDS-PAGE, transferred to nitrocellulose membranes, and incubated with appropriate primary antibodies. After incubating with fluorescence-conjugated secondary antibodies, immunoreactive proteins were visualized by an Odyssey infrared imaging system (LI-COR Biotechnology, Nebraska). Densitometric analysis of the blots was performed with Odyssey software (LI-COR Biotechnology). Results were normalized by arbitrarily setting the densitometry of control samples to 1.0. The antibodies used were GIT1 (Santa Cruz), Notch1 (Santa Cruz), N1-ICD (Millipore), Dll4 (Santa Cruz) Hey1 (Millipore), RBP-J (Santa Cruz), PLCγ (BD Transduction Laboratories), phospho-PLCγ1 (Tyr783) antibody (Cell Signaling) and phospho-p44/42 MAPK (Erk1/2) (Thr202/Tyr204) antibody (Cell Signaling). The immunoprecipitation was performed as published previously (Wang et al., *Arterioscler. Thromb. Vasc. Biol.*, (2008), which is hereby incorporated by reference in its entirety).

Quantitative Reverse Transcriptase PCR Analysis (qRT-PCR).

Total RNA from retinas and lungs of GIT1 WT and KO mice or HUVECs was obtained using TRIzol reagent (Invitrogen) according to the manufacturer's protocol. Genomic/mitochondrial DNA was isolated using Trizol, followed by back extraction with 4 M guanidine thiocyanate, 50 mM sodium citrate, and 1 M tris, and an alcohol precipitation. Target genes mRNA expression and mitochondrial DNA content were determined by qRT-PCR (Applied Biosystems). The sequences of sense and antisense primers, corresponding PCR conditions, and cycle counts were as follows:

D114 (mouse): 5'-CCGCATTTGCCTTAAGCACTTCCA-3' (SEQ ID NO: 23) and 5'-AAATTGAAGGGCAACT-GCAGAGGG-3' (SEQ ID NO: 24);

D114 (human): 5'-CCTGCATTGTGAACACAGCACCTT-3' (SEQ ID NO: 25) and 5'-ACCTGTCCACTTTCT-TCTCGCAGT-3' (SEQ ID NO: 26);

Hey1 (mouse): 5'-GAAACTTGAGTTCGGCGCTGTGTT-3' (SEQ ID NO: 27) and 5'-AGATCCCTGCTTCT-CAAAGGCACT-3' (SEQ ID NO: 28);

Hey1 (human): 5'-AGAGTGCGGACGAGAATG-GAAACT-3' (SEQ ID NO: 29) and 5'-ACCAGCCT-TCTCAGCTCAGACAAA-3' (SEQ ID NO: 30); 30 s at 94° C., 30 s at 55° C., and 30 s at 72° C., 35 cycles. β Actin cDNA was amplified as a control.

Aortic Ring Assay.

This ex vivo angiogenesis assay was performed essentially as described with some modification (Takeshita et al., *Circ. Res.*, 100:70 (2007), which is hereby incorporated by reference in its entirety). Briefly, descending thoracic aortas from GIT1 WT and GIT1 KO mice were harvested and placed in ice-cold M199 medium (Invitrogen). Aortas were flushed with ice-cold M199 medium until free of blood (n=3 from each group). The adventitia was dissected free, and the aorta was cut into multiple 1-mm rings under a dissecting microscope. 24-well culture plates were coated with 400 μL of growth factor-reduced Matrigel (BD Bioscience) per well, then allowed to polymerize for 30 minutes at 37° C. Rings were meanwhile embedded in the growth factor-reduced Matrigel, then supplemented with medium 199, 1% fetal bovine serum, heparin (10 U/mL), antibiotics, and VEGF (50 ng/ml, Peprotech Inc.). Quantitative analysis of endothelial sprouting was performed using images from day 8, and sprout length and sprout area were quantified using ImagePro Plus software (Media Cybernetics Inc, Silver Spring, Md.).

Cell Fractionation.

HUVECs were harvested using buffer A (250 mM Sucrose, 20 mM HEPES, 10 mM KCl, 1.5 mM MgCl2, 1 mM EDTA, 1 mM EGTA) by incubation on ice for 20 minutes followed by shearing through a 25 G needle 10 times. The nuclear pellet was collected by centrifugation for 5 minutes. The supernatant contained membrane and cytoplasmic fractions. The nuclear pellet was washed once with buffer A. The nuclear fraction was sheared through a 25 G needle 10 times and centrifuged again at 3000 rpm for 10 minutes. The nuclear pellet was resuspended in the nuclear buffer (buffer A containing 10% glycerol and 0.1% SDS).

Plasmid cDNA.

Using PCR, GIT1(ANK), GIT1(ΔANK), and GIT1(SHD) were cloned into EGFP-C1 vector.

Luciferase Reporter Assay.

To assess Notch-dependent reporter hairy/enhancer-of-split1(Hey1) luciferase activity, HEK293 cells cultured in a 6-well plate were cotransfected with Hey1 luciferase reporter gene, pCMV-N1-ICD (generous gift from Dr. Eileen M. Redmond), β-galactosidase (β-gal) and GIT1 WT or GIT1 mutants using lipofectamine. After transfection for 20 hours, cells were harvested. The luciferase activity in cell lysates was determined using the Luciferase Reporter Assay kit (Promega) and Wallac 1420 multilabel counter (PerkinElmer). β-gal activity was assayed and used to normalize for differences in transfection efficiency.

Tube Formation.

Tube formation was performed as described before (Pang et al., *Circulation* 1524 (2009), which is hereby incorporated by reference in its entirety).

Sequence Analysis.

The sequence alignment was performed using Uniprot.

Statistical Analysis.

All values are expressed as mean±SE from three to eight independent experiments. Data were assessed using the student's t-test or ANOVA and P<0.05 was considered statistically significant.

Example 1

Impaired Retina Vascular Development and Vessel Sprouting in GIT1 KO Mice

Figures 1A, 1O:
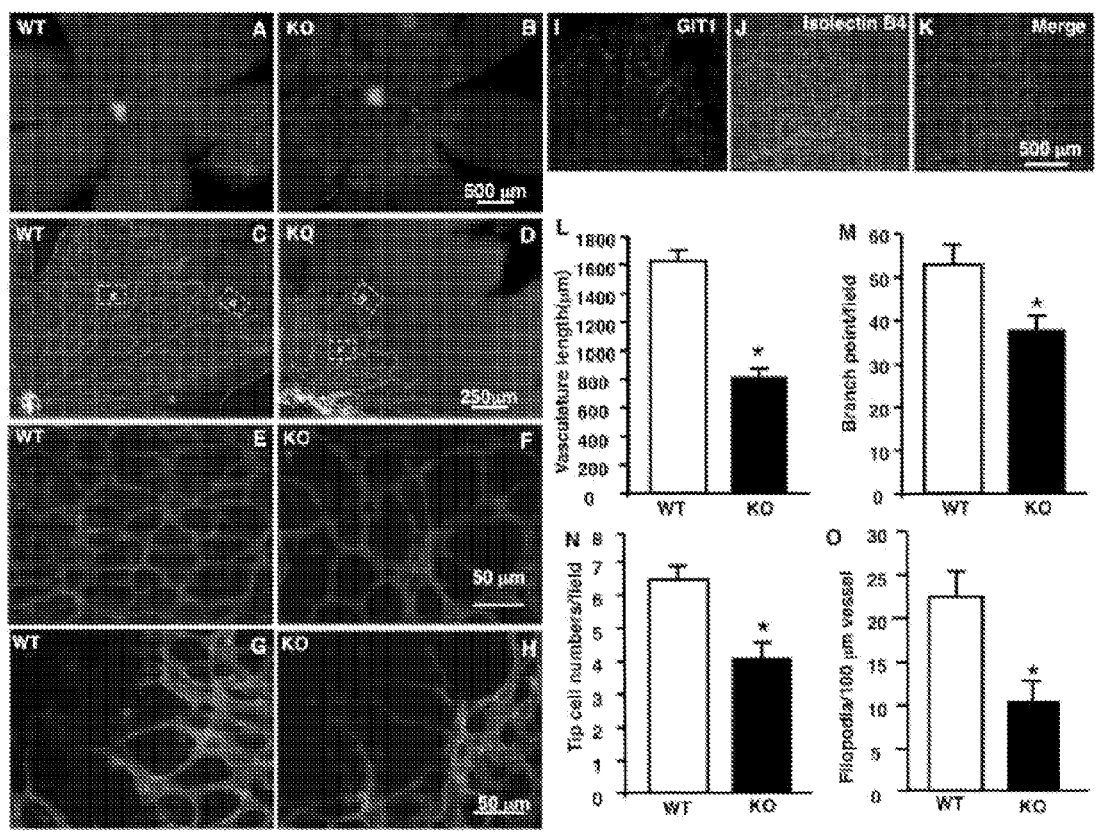
FIGS. 1A-1O show impaired retina vascular development and vessel sprouting in GIT1 KO mice.
Figures 2A, 2B:
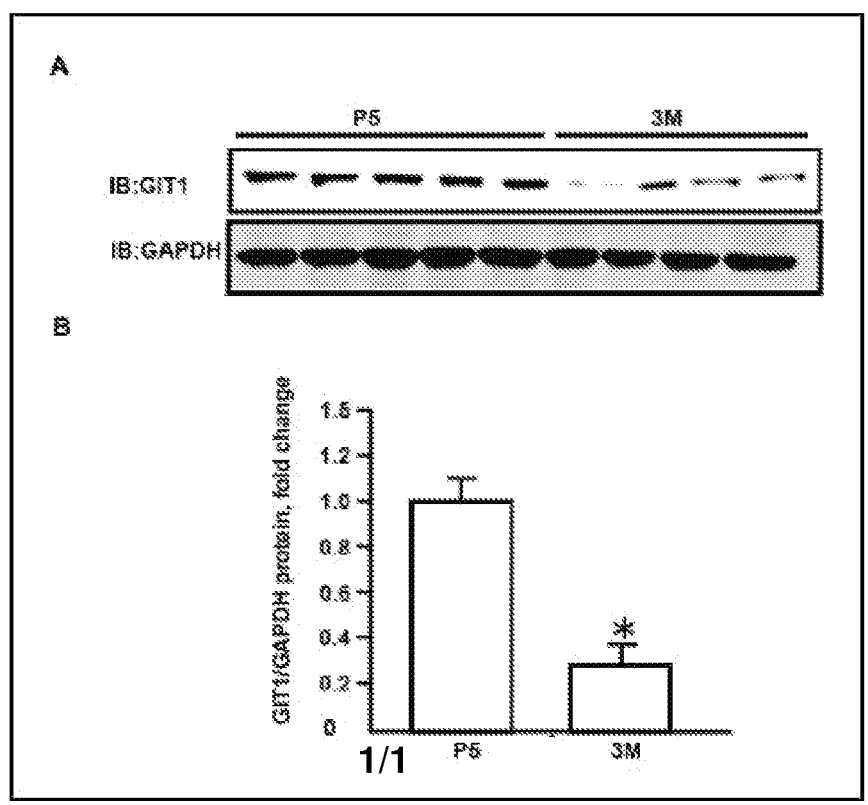
FIGS. 2A-2B show that GIT1 is highly expressed in retinas of P5 mice. Retina tissues of GIT1 WT mice at P5 and 3 months were harvested and total protein was extracted. The expression of GIT1 protein was assayed by western blot (FIG. 2A).
Figures 3A, 3B, 3C, 3D, 3E:
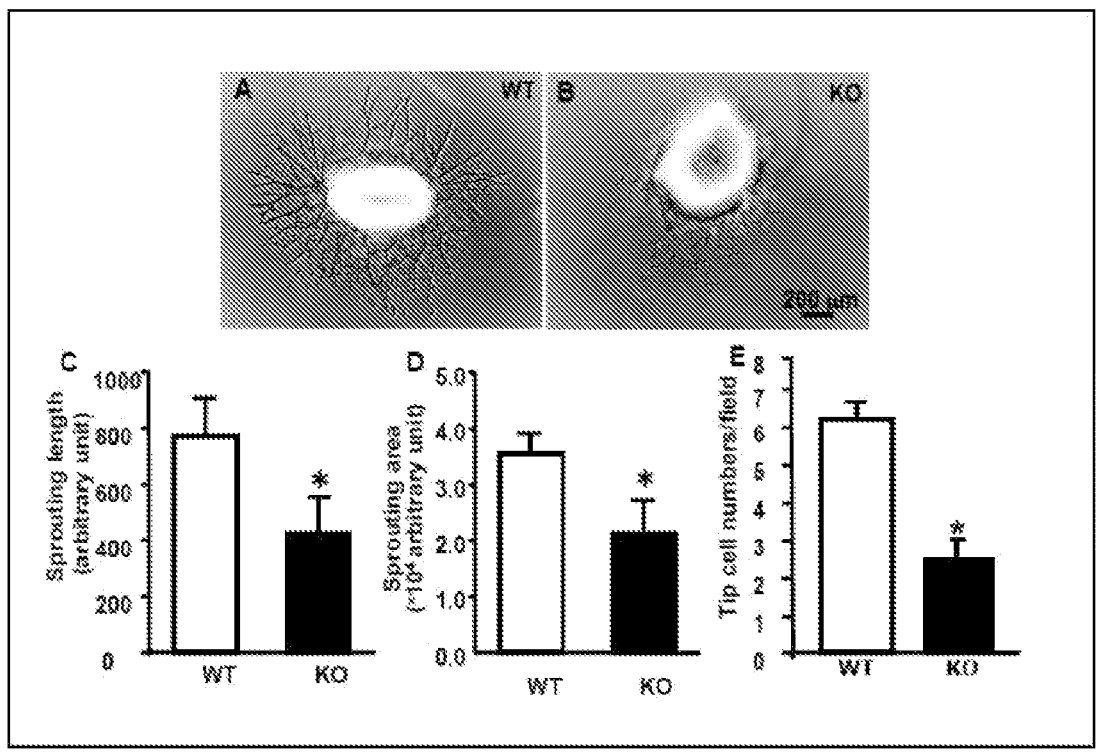
FIGS. 3A-3E are micrographs and bar graphs showing that vessel sprouting was decreased in aorta rings of GIT1 KO mice.

To define the mechanistic role of GIT1 in angiogenesis, the retina vasculature at postnatal day 5 (P5) was visualized by isolectin B4 staining. The retinas of GIT1 KO mice displayed decreases of 49.5±2.1% in vessel length (FIG. 1A-D, L) and 26.4±1.4% in branching point (FIG. 1E-F, M), 37.3±1.8% in tip cells, and 53.2±1.4% in filopodia extension (FIG. 1G-H, N-O). GIT1 expression in P5 retina localized to ECs as measured by isolectin B4 staining (FIG. 1I-K). The highest level of GIT1 was observed in cells at the leading edge of the vascular plexus. Temporal analysis of GIT1 expression showed that there was a 70% decrease in GIT1 expression in adult (3 month) compared to P5 retinas (FIG. 2). To define the role of GIT1 in sprouting angiogenesis, an in vitro endothelial sprouting experiment was performed using GIT1(WT) and KO aortic rings. In GIT1 KO aortas, microvessel sprouting length and sprouting area were significantly reduced compared to GIT1(WT) aortas (45±0.5% and 40±0.4 respectively; p<0.01, FIG. 3A-B). Endothelial tip cell numbers in GIT1 KO aortas were also significantly decreased (58.2±0.8% vs. WT, FIG. 3E). These findings indicate that GIT1 is critical for VEGF induced microvessel sprouting and tip cell formation.

Example 2

Impaired Retina Vascular Development in EC-Specific GIT1 KO Mice

Figures 4A, 4B, 4C:
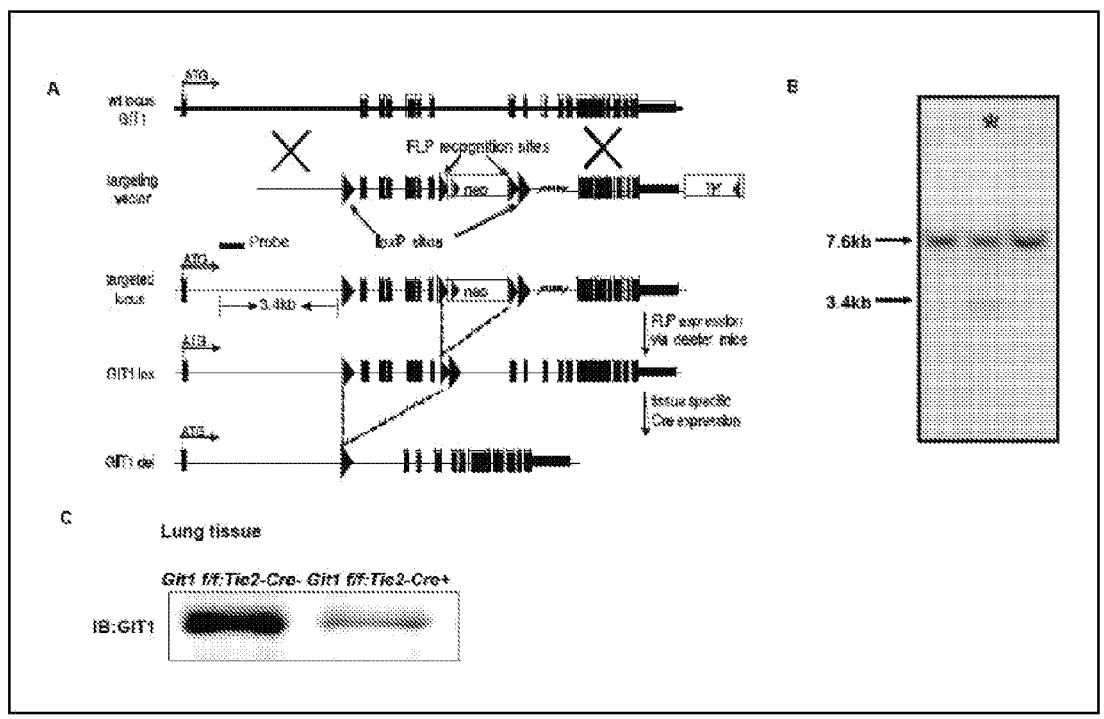
FIGS. 4A-4C illustrate the generation of floxed Git1 mice.
Figures 5A, 5B, 5C, 5D, 5E, 5F, 5G, 5H, 5I, 5J:
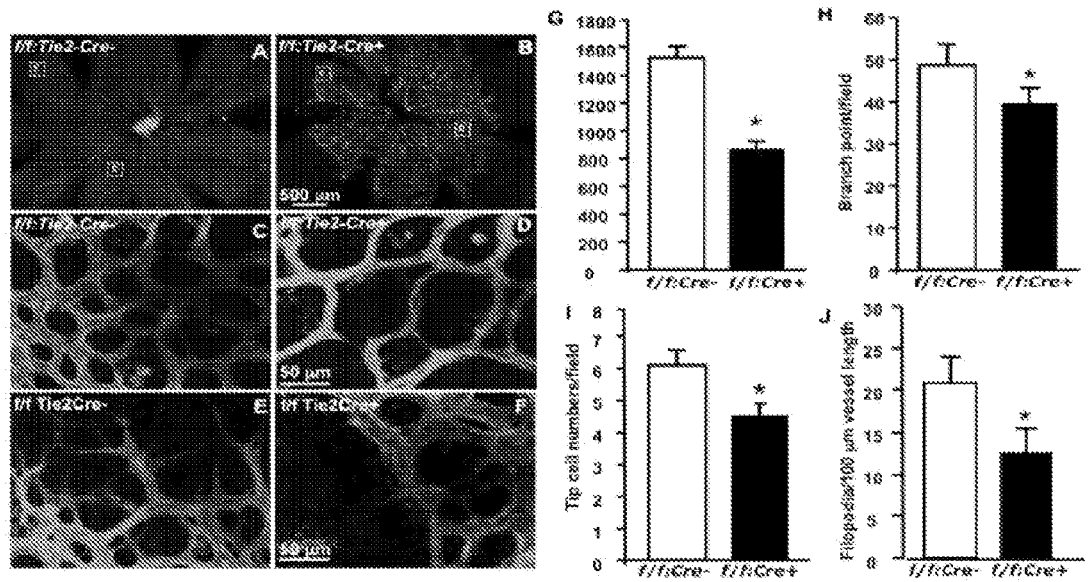
FIGS. 5A-5J show impaired retina vascular development in EC-specific GIT1 KO mice.

To demonstrate the essential role of GIT1 in ECs for postnatal retina vascular development, a floxed Git1 allele was generated and Tie2-Cre was used to conditionally inactivate Git1 in ECs (FIG. 4A-B). GIT1 expression was reduced by approximately 90% (FIG. 4C). Similar to global KO mice, Git1$^{f/f:Tie2-Cre+}$ displayed decreased vessel length, branch points, tip cells and filopodia extensions (FIG. 5). Since the ECs specific GIT1 KO mice phenocopy the global GIT1 KO mice, it appears that GIT1 expression in ECs is required for angiogenesis.

Example 3

GIT1 Depletion Enhances Dll4-Notch1 Feedback Loop In Vivo

Endothelial tip cell and filopodia numbers are tightly regulated by the VEGF-Notch-Dll4 pathway. The pathway is controlled by a feedback loop in which VEGF activates Notch1 which then increases Dll4 expression (Liu et al., Mol. Cell Biol., 23:14 (2003); Williams et al., Blood 107:931 (2006), each of which is hereby incorporate by reference in its entirety). Dll4 in turn activates Notch1 signaling in neighboring cells. This feedback acts as a negative regulator of VEGF signaling by inhibiting VEGF receptor 2 (VEGFR2) expression and is essential for the formation of a stable vascular plexus (Suchting et al., Proc. Natl. Acad. Sci. 104:3225 (2007), which is hereby incorporated by reference in its entirety). Because Dll4 is localized prominently in ECs at the leading front of the superficial retinal plexus (Hofmann et al., Circ. Res. 100:1556 (2007), which is hereby incorporated by reference in its entirety), and altering Dll4 expression dramatically changes EC tip cell and filopodia numbers, regulation of Dll4 is particularly important (Lobov et al., Proc. Natl. Acad. Sci. 104:3219 (2007); Suchting et al., Proc. Natl. Acad. Sci. 104:3225 (2007); Hellstrom et al., Nature 445:776 (2007), each of which is hereby incorporated by reference in its entirety). Dll4 protein expression was increased 5.0±0.3 fold in retinas and 6.0±0.6 fold in lungs of GIT1 KO mice compared to WT mice (FIG. 6A-D, P<0.01). Similarly, Dll4 mRNA expression (FIG. 7) in both lungs and retinas of GIT1 KO mice was significantly increased. These data show a critical role of GIT1 in the regulation of Dll4 expression in pulmonary and retina vascular development.

Example 4

GIT1 Depletion Enhances Dll4-Notch1 Feedback Loop In Vitro

Figures 6A, 6B, 6C, 6D, 6E, 6F, 6G, 6H, 6I, 6J, 6K:
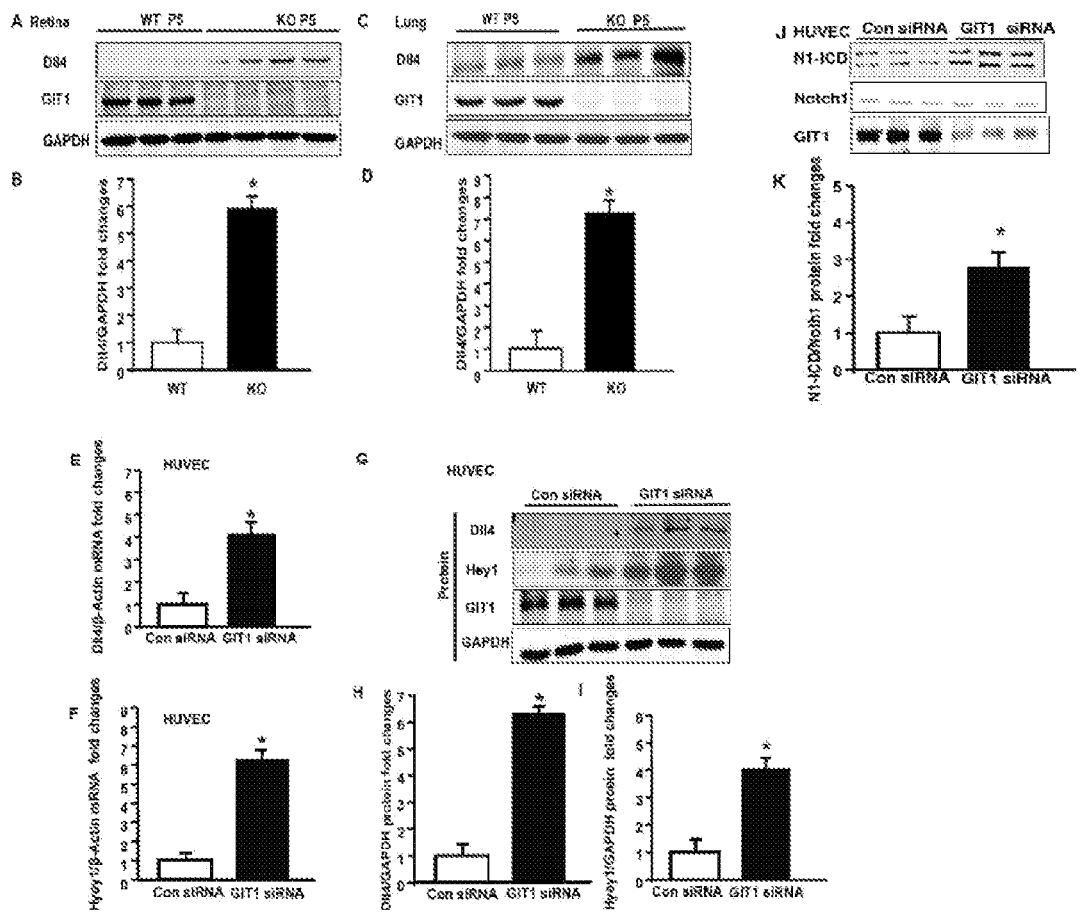
FIGS. 6A-6K show that GIT1 depletion enhances Dll4-Notch1 feedback loop in vivo and in vitro.
Figures 7A, 7B:
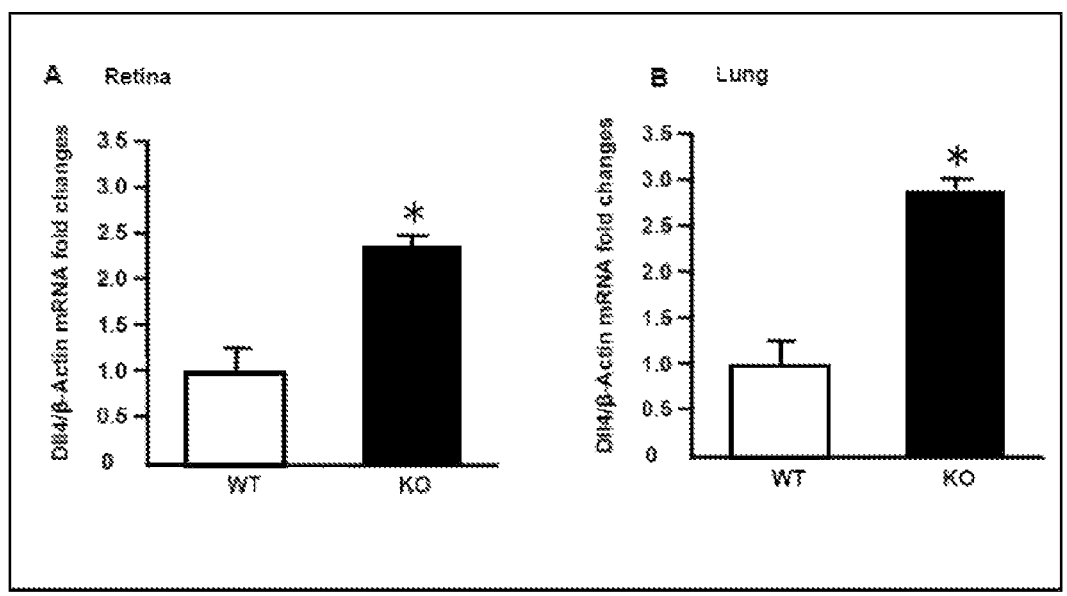
FIGS. 7A-7B are bar graphs showing enhanced Dll4 mRNA expression in retinas and lungs of GIT1 KO mice. The retinas and lungs of GIT1 WT and KO mice at P5 were harvested and total mRNA was extracted by Trizol. Dll4 mRNA expression was assayed by qRT-PCR, and the graphs show quantitiation of the relative change of Dll4 mRNA expression in tissues of GIT1 KO compared to WT mice (Dll4 expression normalized to β-Actin in WT group). *P<0.05 compared with WT groups (mean±SE; n=3).

Based on these in vivo data, it was hypothesized that GIT1 inhibited the Dll4-Notch1 feedback loop. To test this hypothesis, the effect of GIT1 on Dll4-Notch1 signaling was assayed in human umbilical vein endothelial cells (HUVECs). In the canonical Notch signaling pathway, upon ligand (Delta and Serrate/Jagged) binding, Notch1 is proteolytically cleaved by γ-secretase to generate the Notch intracellular domain (N1-ICD). Upon N1-ICD formation, it translocates to the nucleus, where it binds to recombining binding protein suppressor of hairless (RBP-J, a known repressor of Notch angiogenesis signaling) and regulates gene expression (Phng et al., Dev. Cell 16:196 (2009); Roca et al., Genes Dev. 21:2511 (2007), each of which is hereby incorporated by reference in its entirety. It is known that Dll4 is highly expressed in confluent ECs (Zhang et al., J Biol. Chem. 286:8055 (2011), which is hereby incorporated by reference in its entirety). Therefore HUVECs were transfected with control or GIT1 siRNA for 48 h. Similar to the in vivo data, Dll4 mRNA and protein expression significantly increased by 3.2±0.6 and 6.3±0.3 fold respectively in GIT1 siRNA compared to control siRNA (FIGS. 3E, G, H; P<0.05. N=3). Analysis of the RBP-J target gene Hairy/enhancer-of-split related with YRPW motif protein 1 (Hey1), showed that its expression pattern was similar to Dll4 with significant increases in mRNA and protein expression after GIT1 depletion (5.2±0.57 and 3.0±0.3 fold, P<0.05; FIGS. 6F, G, I). The effect of GIT1 on basal Notch1 expression and cleavage was studied next. In GIT1 siRNA treated HUVECs, there was no change in Notch1 expression (FIG. 6J). However, expression of N1-ICD in GIT1 siRNA treated HUVECs was significantly enhanced 1.7±0.4 fold (FIG. 6J-K). The increase of N1-ICD is consistent with the increased expression of Notch ligand Dll4 shown in FIG. 6E, G-H.

Example 5

Figures 8A, 8B, 8C, 8D, 8E, 8F, 8G, 8H, 8I, 8J, 8K, 8L, 8M:
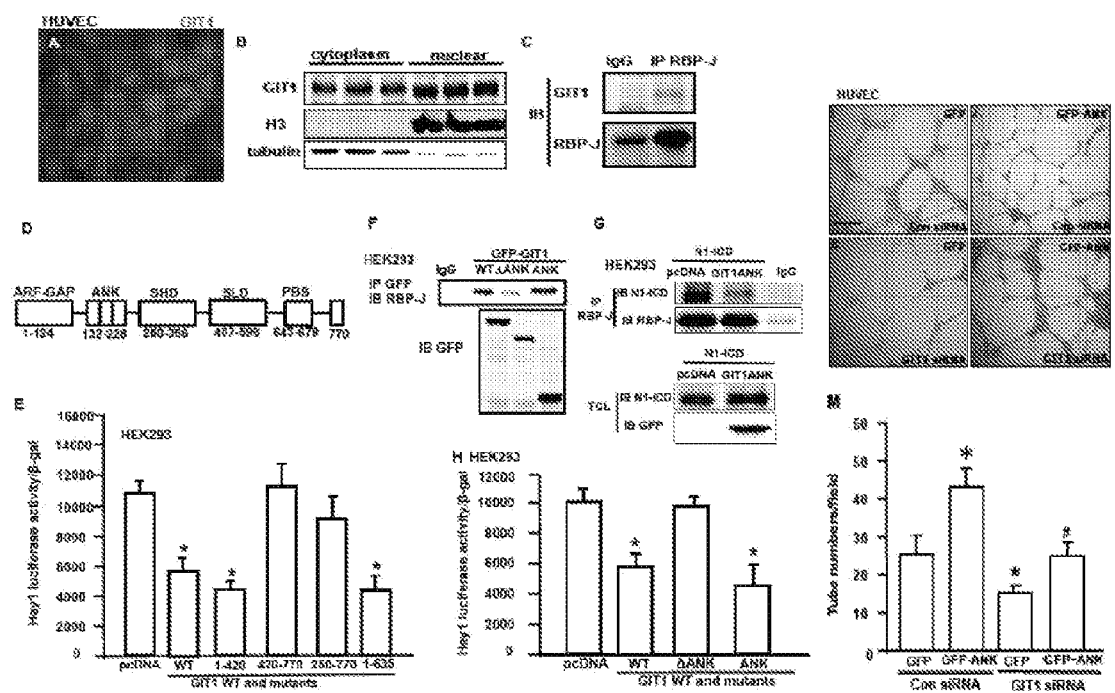
FIGS. 8A-8M show the ankyrin repeat domain is indispensible for the effect of GIT1 on Notch signaling and angiogenesis.

Ankyrin Repeat Domain is Indispensible for the Effect of GIT1 on Notch Signaling and Angiogenesis A likely target for GIT1 inhibition of Dll4-Notch1 signaling is RBP-J, a known repressor of Notch signaling (Phng et al., Dev. Cell 16:196 (2009); Gridley, Development 134: 2709 (2007), each of which is hereby incorporated by reference in its entirety). GIT1 localized to the nucleus by both immunohistochemistry and cell fractionation (FIG. 8A-B). Furthermore, GIT1 co-immunoprecipitated with RBP-J in HUVECs (FIG. 8C).

Figure 10:
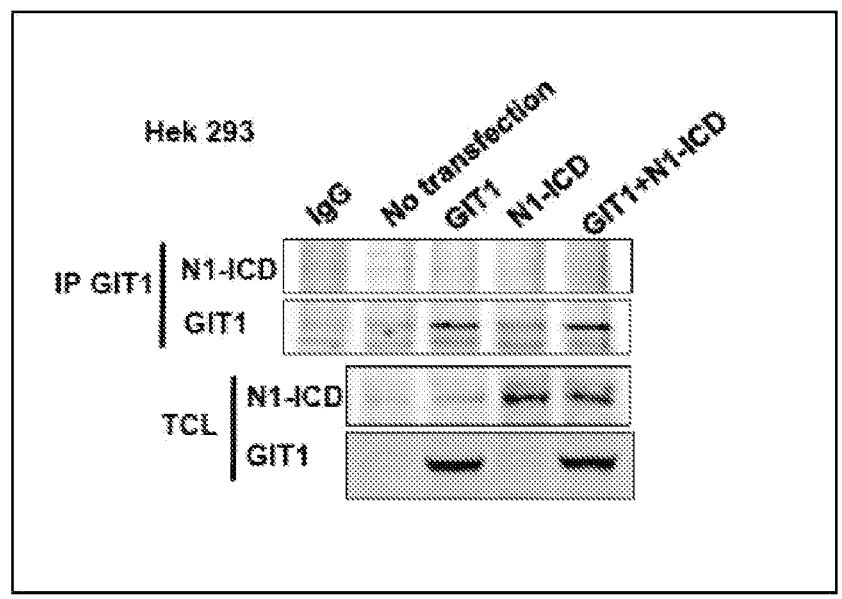
FIG. 10 shows that GIT1 does not associate with N1-ICD. HEK293 cells were transfected with Xpress-GIT1 (wt) or N1-ICD either singly or together for 24 h. GIT1 was immunoprecipitated (IP) with anti-GIT1 antibody. The immunoprecipitates were then immunoblotted (IB) using anti-N1-ICD antibody or GIT1 antibody.

To identify the specific domains of GIT1 required for the regulation of Notch signaling, the effects of several GIT1 domain deletion mutants on expression of Hey1 (a Notch target gene) induced by N1-ICD were studied. As a model system, HEK293 cells were used since they express almost no GIT1 (Pang et al., Arterioscler. Thromb. Vasc. Biol. 28:892 (2008), which is hereby incorporated by reference in its entirety). Transfection of GIT1(WT) decreased Hey1 luciferase activity by 50% (FIGS. 8D, E; n=3, p<0.05). Similarly, GIT1 (1-420) and GIT1(1-635) significantly decreased Hey1 luciferase activity by 65% and 66%, respectively. In contrast, GIT1 (420-770) and GIT1 (250-770) had no significant effect. Based on these data, domain(s) present in GIT1 (1-250) are critical for GIT1 mediated N1-ICD transcriptional effects. There are two known functional domains in GIT1 (1-250), the ARF-GAP domain (1-124) and the ankyrin repeat domain (132-228, FIG. 8D). The ankyrin repeat domain contains a motif of 33 amino acid residues and was first identified in the sequence of Notch (Drosophila) (Kohl et al., Proc. Natl. Acad. Sci. 100:1700 (2003); Breeden et al., Nature 329:651 (1987), each of which is hereby incorporated by reference in its entirety). There are several highly conserved amino acids (TPLH) in ankyrin repeats, and these amino acids are essential for the helix turn-helix conformation and protein-protein interactions (FIG. 9) (Mosavi et al., Proc. Natl. Acad. Sci. 99:16029 (2002); Sedgwick et al., Trends Biochem. 24:311 (1999); Mosavi et al., Protein Sci. 13:1435 (2004), each of which is hereby incorporated by reference in its entirety). Although a recent sequence homology analysis demonstrated 3,608 proteins containing ankyrin repeat domains, protein-protein interactions dependent on ankyrin repeats are specific with limited numbers of binding partners (Mosavi et al., Protein Sci. 13:1435 (2004), which is hereby incorporated by reference in its entirety). To determine whether GIT1 interacts with N1-ICD through ankyrin repeat domain, GIT1(WT) and N1-ICD were co-expressed in HEK293 cells. There was no association when GIT1 was immunoprecipitated (FIG. 10). It has also been established that N1-ICD interacts with RBP-J through two domains; the ankyrin repeats and the RBP-J associated module (Tani et al., *Nucleic Acids Res.* 29:1373 (2001), which is hereby incorporated by reference in its entirety). To study the interaction between GIT1 and RBP-J, we expressed GIT1(WT) and two ankyrin repeat (ANK) mutants; GIT1(ΔANK, missing AA132-228), and GIT1(ANK, expressing AA132-228) in HEK293 cells transfected with N1-ICD. As anticipated, GIT1(WT) and GIT1 (ANK) strongly associated with RBP-J, while GIT1 (ΔANK) associated weakly with RBP-J (FIG. 8F). Expression of GIT1 (ANK) significantly decreased the binding of N1-ICD with RBP-J (FIG. 8G). To confirm the effect of GIT1(ANK) on Notch signaling, Hey1 expression was measured after transfection of GIT1(WT) and the ankyrin mutants. GIT WT and GIT1(ANK) significantly decreased Hey1 expression by 42% and 58%, whereas GIT1(ΔANK) had no significant effect (FIG. 8H). Based on these data, it is proposed that GIT1 binds to RBP-J through the ankyrin repeat domain and prevents RBP-J binding to N1-ICD, presumably by steric hindrance (FIG. 11). Most importantly, overexpression of GIT1-ANK restored impaired angiogenesis arising from the depletion of GIT1 (FIG. 8I-8M).

Figures 11A, 11B:
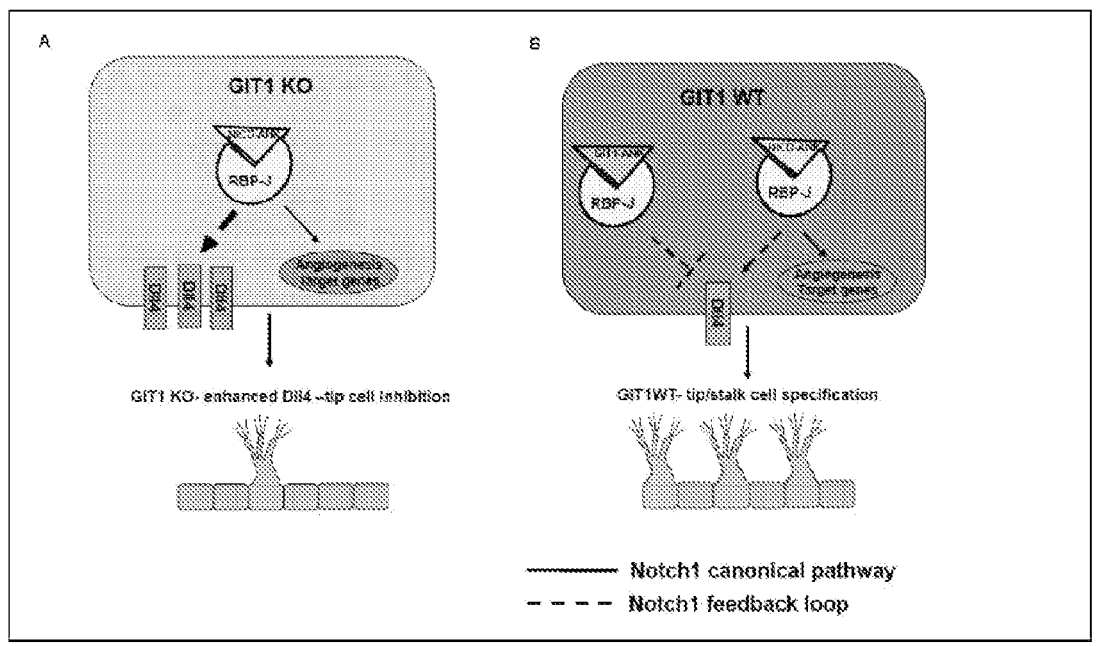
FIGS. 11A-11B are illustrations depicting how the presence or absence of GIT1 affects angiogenic processes. The illustration in FIG. 11A depicts that in GIT1 KO cells, the balance of the canonical and feedback loop is interrupted. RBP-J only binds to N1-ICD, and Dll4 expression is dramatically enhanced. The tip cells switch to stalk cells and sprouting angiogenesis is impaired. The illustration in FIG. 11B shows that in GIT1 WT cells, N1-ICD binds to RBP-J which increases Notch target gene expression and tip cell formation (canonical Notch1 pathway). RBP-J also associates with GIT1 through competition with N1-ICD, which subsequently inhibits Dll4-Notch feedback loop. As a consequence of the synergistic effects of the canonical and the feedback loop, the sprouting angiogenesis precedes normally.

Previously it has been shown that GIT1 was required for VEGF stimulation of phospholipase Cγ (PLCγ) and ERK1/2, and modulated EC migration and cell proliferation (Pang et al., *Circulation* 1524 (2009); Yin et al., *Mol. Cell Biol.* 24:875 (2004); Za et al., *J Cell Sci.* 119:2654 (2006), each of which is hereby incorporated by reference in its entirety). These critical functions of GIT1 contribute to the abnormal phenotypes observed in the lung and bone of GIT1 KO mice (Pang et al., *Circulation* 1524 (2009); Menon et al., *J Cell Physiol.* 225:777 (2010), each of which is hereby incorporated by reference in its entirety). However, the effect of GIT1 on Notch signaling is probably not due to PLCγ and ERK1/2 pathways, since previous data demonstrated that GIT1 interacts with PLCγ and MEK1-ERK1/2 through the Spa homology domain (SHD), not the ankyrin repeat domain. The major finding in this example is that GIT1 is a novel regulator of Notch1 signaling in EC. GIT1 deficiency leads to increased Dll4 expression associated with decreased tip cell formation and sprouting angiogenesis (FIG. 11A). Because GIT1ANK binds to RBP-J, as does the ankyrin repeat domain of N1-ICD, it is believed that under normal physiological conditions GIT1 regulates Notch signaling by controlling Dll4 expression by competing with N1-ICD (FIG. 11B). GIT1 regulation of Dll4 is particularly powerful for angiogenesis, because Dll4 determines tip cell and stalk cell specification, both due to its trans function (Dll4 interacts with Notch1 of neighboring cell) and its cis function (Dll4 interacts with Notch1 in the same cell and inhibits Notch signaling) (Sprinzak et al., *Nature* 465:86 (2010), which is hereby incorporated by reference in its entirety). Due to the important role of Notch-Dll4 feedback loop in physiological and pathological angiogenesis, specific inhibitors of Notch1 and Dll4 have been proposed as therapeutic targets for angiogenesis related diseases (Lobov et al., *Proc. Natl. Acad. Sci.* 104:3219 (2007); Ridgway et al., *Nature* 444:1083 (2006), each of which is hereby incorporated by reference in its entirety). Future studies of GIT1(ANK) as a tool to regulate angiogenesis will be very informative.

Example 6

Overexpression of GIT1(SHD) Inhibits PLCγ Activation Induced by VEGF

The spa homology domain (SHD) of GIT1 is essential for several GIT1 mediated signaling pathways that are induced by tyrosine kinase receptor (TKR) and other growth factors, including PLCγ, MEK1-ERK1/2 and Rac1/cdc42. These signaling pathways are important for EC proliferation, migration and tube formation, which are also major steps during angiogenesis. Most importantly, GIT1 and its ortholog GIT2 are the only proteins in the mammalian genome that contain a SHD. The GIT2-KO has no defects in vasculature development suggesting that the GIT1-SHD is unique.

In an effort to identify the potential GIT1 inhibitor peptides, a flag-tagged SHD domain of GIT1 (SHD-Flag) was cloned into a lentivirus vector. Since it was previously demonstrated that GIT1 interacts with PLCγ and MEK1-ERK1/2 through the SHD, the effect of overexpression of this domain on the ability of VEGF to activate PLCγ was tested.

HUVECs were seeded on 6 well plate at 80% confluence. The next day, cells were infected with control and SHD-Flag containing Lentivirus with Polybrene. After 1 day, infection media was changed with fresh complete M200 media (containing 5% FBS+1% Penicillin-Streptomycin and 2% LSGS). After 48 hours, cells were serum starved with serum free M200 media for 1 hour and stimulated with VEGF (10 ng/mL) for different time points ranging from 0 to 30 minutes. Next cells were lysed and used for western blot analysis to measure PLCγ and ERK1/2 activation. VEGF treatment induced PLCγ activation after 2 minutes of treatment while overexpression of flag tagged SHD blocked VEGF induced PLCγ activation in HUVEC. No effect of SHD overexpression on VEGF induced ERK1/2 activation was observed. Flag tagged SHD expression in HUVECs were confirmed by detecting Flag in the lysate In addition to PLCγ signaling, the effect of SHD overexpression on HUVEC tube formation in vitro was also assessed. Endothelial cells reorganize themselves in a 3D matrix like matrigel and form tubes which is an index of in vitro angiogenesis. After 48 hours, cells were cultured at a constant number (104 cells/well) with VEGF on growth factor reduced matrigel (30 uL) coated 96 well plate and incubated for 16 hours. SHD overexpression inhibited the formation of tube-like structures by HUVECs compared to control treatment groups.

This data demonstrates that overexpression of GIT1-SHD significant decreased PLCγ activation and tube formation in response to VEGF. These finding indicate that GIT1-SHD domain is a potential drug target of angiogenesis related diseases Materials and Methods for Examples 7-13

Lentiviral Virus Preparation and Infection pLV-CMV-IRES-GFP is an HIV-1 based lentiviral expression vector that allows simultaneous expression of GIT1-ANK and EGFP from the CMV promoter. Infectious viral particles were generated by co-transfection of the transgene, with plasmids expressing viral gag/pol genes (psPAX2) and VSV-G coat protein (pMD2.G) into HEK293T cells using Fugene6 (Promega). Forty-eight to seventy-two hours post-transfection viral containing supernatants were collected, filtered through 0.45 μm cellulose acetate filters and stored in aliquots at −80° C. For viral concentration, supernatants were spun at 25,000 rpm in a SW28 rotor for 2 h at 4° C. and the viral pellet resuspended in 200 μl of HBSS.

HUVECs were grown to 70% confluence in 6 well plate. Lentiviral particles were mixed with 8 μg of Polybrene (hexadimethrine bromide) in complete M200 media and then added to the HUVECs and incubated for 48 h at 5% $CO_2/37°$ C. After 48 h of infection, cells were used for functional and biochemical studies.

Generating ANK Peptide Using Interpro Tools.

Interpro was used to design a GIT1-ANK blocking peptide having the amino acid sequence of GTTPLHVAAK-AGQ (called ANK-Active ANK peptide; SEQ ID NO: 31). In addition to the blocking peptide, a peptide having a scrambled amino acid sequence of TLQAELLVVYGA (called sANK-Scrambled ANK peptide; SEQ ID NO: 32) was also designed as a control peptide. The HIV-1 TAT sequence YGRKKRRQRRR (SEQ ID NO: 33) was added to the front end of both the active ANK peptide and the scrambled ANK peptide sequences to achieve cell permeabilization. The peptides were synthesized by Biomatik USA, Delaware, USA.

Western Blot Analysis.

Cells were harvested and lysed in lysis buffer (20 mM Tris-HCl (pH 7.5), 150 mM NaCl, 1 mM Na2EDTA, 1 mM EGTA, 1% Triton, 2.5 mM sodium pyrophosphate, 1 mM b-glycerophosphate, 1 mM Na3VO4, 1 µg/ml leupeptin, Cell Signaling) with protease inhibitor cocktail. Protein concentration was determined by Bradford assay (Bio-Rad), and cell lysates were subjected to SDS-polyacrylamide gel electrophoresis (PAGE). Proteins were then transferred onto nitrocellulose membranes, and the membranes were subsequently blocked with 5% milk in PBST for 1 hour. Blots were incubated overnight at 4° C. with appropriate primary antibodies. After being washed 3 times with PBS/0.1% Tween20, membranes were incubated with HRP conjugated secondary antibodies for 1 hour. Blots were developed using the ECL technique. Densitometry analysis was performed using the Image J software.

Matrigel Plug Angiogenesis Assay.

Matrigel (250 µL) containing VEGF (50 ng/mL) with lenti-virus vector/lenti-GIT1-ANK and sANK/ANK peptide (75 µM) were injected subcutaneously on the ventral side of the mouse in the groin area close to the dorsal midline, vector or sANK peptide on left center of back, and GIT1-ANK or ANK peptide on right center of back. Seven days after injections, matrigel plugs were harvested, fixed with 10% neutral buffered formalin, sectioned and processed for hematoxylin and eosin staining (HE staining) Vessel density was evaluated by von Willebrand factor (vWF), and infection efficiency of lentivirus was detected by green fluorescent protein (GFP) staining.

Endothelial Tube Formation Assay.

Growth Factor reduced Matrigel (BD Bioscience 354230) was thawed overnight at 4° C. Each well of 96 well plates were coated with 40 µL of matrigel and kept in the 37° C. incubator for 30 minutes for gelatinization. HUVEC at P4 were harvested and suspended in non-supplemented Medium 200. The concentration of the cells was determined by hemocytometer counting technique. HUVECs (3000) in suspension with 30 µM ANK peptide and 50 ng/mL VEGF were loaded per 96 well and incubated at 37° C., 5% $CO_2$ overnight. The following day, formed tubes were imaged under 4× objective of the microscope and analyzed using Image J software.

Example 7

Overexpression of ANK in HUVEC Increases Dll4 Protein Expression

HUVEC were plated on 6 well plates at 90% confluence and incubated overnight. Cells were treated with Lenti-vector or Lenti-ANK and incubated for 24 hour at 37° C., 5% $CO_2$. Cells were lysed and western blotting was performed to measure the Dll4 protein expression. ANK overexpression in HUVEC increased Dll4 protein expression by 1.6 fold compared to vector treated cells (FIGS. 13A-13B).

Example 8

ANK Lenti-Virus Treatment Blocks In Vivo Angiogenesis

Matrigel plugs were generated by subcutaneous injection of 250 µl matrigel containing lenti-GFP and lenti-GFP-ANK in GIT1-WT mice. After 7 days, plugs were harvested and imaged. Paraffin embedded sections of the plugs were stained for hematoxylin and eosin. FIGS. 14B and 14D show that Lenti-ANK inhibited angiogenesis in the matrigel plugs as compared to control lenti-vector (FIGS. 14A and 14C). Further analysis by counting the number of vessels per unit area of the plugs demonstrated 84% reduction in vessels density in plugs treated with Lenti-GFP ANK (black bar in FIG. 14E) compared to plugs treated with lenti-GFP (white bar in FIG. 14E).

The Notch signaling system is extremely complex. Therefore, while these in vivo results appear somewhat inconsistent with the in vitro angiogenesis data of FIG. 8M, where GFP-ANK transfection of HUVECs did not appear to inhibit tube formation, this can be explained by the limitations of the in vitro system and its failure to fully recapitulate the complexity of the in vivo Notch signaling system.

Example 9

ANK Lenti-Virus Treatment Rescues Impaired Angiogenesis in GIT1-KO Mice

The effects of lenti-GIT1-ANK on angiogenesis in GIT1-KO mice was also assessed using VEGF containing matrigel plugs. There was a significant increase in vessel number in lenti-GIT1-ANK treated plugs compared to lenti-vector treated plugs both on gross appearance (compare FIGS. 15A-15B) and in H&E histochemistry (compare FIGS. 15C-15D). vWF immunohistochemistry demonstrated a 45% increase in vessel density of lenti-GIT1-ANK compared to lenti-vector (compare FIGS. 15E-15F, and 15I). GFP staining showed successful infection of lenti-vector and lenti-GIT1-ANK (FIGS. 15G-15H), infection efficiency was greater than 90%.

Example 10

ANK Peptide Increases Dll4 Protein Expression in HUVEC

HUVEC were plated in 6 well plate at 90% confluence and incubated overnight at 37° C., 5% $CO_2$. Cells were treated with 15 µM sANK and ANK peptide and incubated for 24 hours. ANK treatment increased Dll4 expression by 2.7 fold compared to sANK treated controls as shown in the Western blot of FIG. 16A. Quantitation of the expression in shown in the graph of FIG. 16B.

Example 11

ANK Peptide Attenuates VEGF Induced Tube Formation in HUVEC

To study the effect of ANK peptide on in vitro angiogenesis, tube formation assays were performed. ANK peptide treatment inhibited tube formation by 59% compared to sANK treated controls (FIGS. 17A-17C).

Example 12

ANK Peptide Inhibits Angiogenesis In Vivo

Matrigel plugs were generated by subcutaneous injection of 250 μL matrigel containing sANK and ANK (75 μM) in C57 mice. Plugs were harvested and imaged. The images showed significant inhibition of peripheral vascular structures in the plugs treated with ANK peptide compared to sANK treated controls (compare FIGS. 18A (sANK) and 18B (ANK)). Plugs were fixed and embedded in paraffin. Paraffin embedded tissue sections were stained with hematoxylin and eosin which demonstrated significant reduction in number of invaded endothelial cells in the plugs of ANK peptide treated sets (compare FIGS. 18C (sANK) and 18D (ANK)).

Example 13

ANK Peptides Inhibit VEGF Induced PLCγ Activation in HUVEC

HUVECs were plated on 6 well tissue culture plates and grown overnight. The following day, cells were treated with 15 μM of sANK and ANK peptide for 4 hours in low serum media. After 4 hours, cells were stimulated with 10 ng/mL of VEGF for different time points. Cells were lysed for western blot to measure ERK1/2 and PLCγ activation. A significant inhibition of VEGF induced PLCγ activation at 15 and 30 minutes in ANK treated HUVEC was observed (FIGS. 19A-19B). In contrast, ANK peptide treatment did not affect VEGF induced ERK1/2 activation (FIG. 19A-19B).

---

What is claimed is:

1. A method of inhibiting angiogenesis in a subject comprising:
   selecting a subject having a condition associated with abnormal angiogenesis and
   administering a G-protein-coupled receptor kinase interacting protein-1 (GIT1) inhibitor to the selected subject, wherein the GIT1 inhibitor is (i) an antibody or antigen-binding portion thereof that binds to at least a portion of an amino acid sequence of SEQ ID NO: 8, or (ii) a peptide comprising the amino acid sequence of SEQ ID NO: 17 or SEQ ID NO: 18, under conditions effective to inhibit angiogenesis in the selected subject.

2. The method of claim 1, wherein the condition associated with abnormal angiogenesis is selected from the group consisting of cancer, macular degeneration, and pulmonary arterial hypertension.

3. The method of claim 1, wherein the at least a portion of the amino acid sequence of SEQ ID NO: 8 bound by the antibody or antigen-binding portion thereof comprises an ankyrin repeat domain sequence (TPLH) of SEQ ID NO: 8.

4. The method of claim 1, wherein the antibody or antigen-binding portion thereof binds to at least a portion of an amino acid sequence selected from the group consisting of SEQ ID NO: 2, SEQ ID NO:3, SEQ ID NO:4, SEQ ID NO:5, and SEQ ID NO: 6.

5. The method of claim 1, wherein the GIT1 inhibitor is administered via a delivery vehicle.

6. The method of claim 5, wherein the delivery vehicle is selected from the group consisting of viral vectors, biodegradable microspheres, microparticles, nanoparticles, liposomes, collagen minipellets, and cochleates.

7. The method of claim 6, wherein the delivery vehicle is a nanoparticle.

8. The method of claim 1, wherein the GIT1 inhibitor is coupled to an endothelial cell-targeting moiety.

9. The method of claim 8, wherein the endothelial cell-targeting moiety is an endothelial cell surface receptor ligand selected from the group consisting of vascular endothelial growth factor (VEGF), fibroblast growth factor (FGF), integrin, fibronectin, intracellular adhesion molecule (ICAM), platelet derived growth factor (PDGF), P-selectin ligand, vascular cell adhesion molecule (VCAM-1) ligand, and ICAM-1 ligand.

10. The method of claim 8, wherein the endothelial cell-targeting moiety comprises a tripeptide sequence of Arg-Gly-Asp (RGD) or Asn-Gly-Arg (NGR).

11. The method of claim 1, wherein the GIT1 inhibitor is administered via a nanoparticle delivery vehicle coupled to an endothelial cell-targeting moiety.

12. The method of claim 1, wherein the GIT1 inhibitor is coupled to a cell-penetrating moiety.

13. The method of claim 12, wherein the cell-penetrating moiety comprises a trans-activator of transcription (TAT) peptide.

* * * * *

UNITED STATES PATENT AND TRADEMARK OFFICE
CERTIFICATE OF CORRECTION

PATENT NO. : 9,670,259 B2
APPLICATION NO. : 14/775936
DATED : June 6, 2017
INVENTOR(S) : Berk et al.

It is certified that error appears in the above-identified patent and that said Letters Patent is hereby corrected as shown below:

In the Specification

Column 1 Lines 12-14, delete "This invention was made with government support under grant number HL63462 awarded by National Institutes of Health. The government has certain rights in this invention." and insert -- This invention was made with government support under grant number HL063462 awarded by the National Institutes of Health. The government has certain rights in the invention. --

Signed and Sealed this
Twentieth Day of February, 2018

Andrei Iancu
*Director of the United States Patent and Trademark Office*

SEQUENCE LISTING

<160> NUMBER OF SEQ ID NOS: 33

<210> SEQ ID NO 1
<211> LENGTH: 761
<212> TYPE: PRT
<213> ORGANISM: Homo sapiens

<400> SEQUENCE: 1

```
Met Ser Arg Lys Gly Pro Arg Ala Glu Val Cys Ala Asp Cys Ser Ala
1               5                   10                  15

Pro Asp Pro Gly Trp Ala Ser Ile Ser Arg Gly Val Leu Val Cys Asp
            20                  25                  30

Glu Cys Cys Ser Val His Arg Ser Leu Gly Arg His Ile Ser Ile Val
        35                  40                  45

Lys His Leu Arg His Ser Ala Trp Pro Pro Thr Leu Leu Gln Met Val
    50                  55                  60

His Thr Leu Ala Ser Asn Gly Ala Asn Ser Ile Trp Glu His Ser Leu
65                  70                  75                  80

Leu Asp Pro Ala Gln Val Gln Ser Gly Arg Arg Lys Ala Asn Pro Gln
                85                  90                  95

Asp Lys Val His Pro Ile Lys Ser Glu Phe Ile Arg Ala Lys Tyr Gln
            100                 105                 110

Met Leu Ala Phe Val His Lys Leu Pro Cys Arg Asp Asp Asp Gly Val
        115                 120                 125

Thr Ala Lys Asp Leu Ser Lys Gln Leu His Ser Ser Val Arg Thr Gly
    130                 135                 140

Asn Leu Glu Thr Cys Leu Arg Leu Leu Ser Leu Gly Ala Gln Ala Asn
145                 150                 155                 160

Phe Phe His Pro Glu Lys Gly Thr Thr Pro Leu His Val Ala Ala Lys
                165                 170                 175

Ala Gly Gln Thr Leu Gln Ala Glu Leu Leu Val Val Tyr Gly Ala Asp
            180                 185                 190

Pro Gly Ser Pro Asp Val Asn Gly Arg Thr Pro Ile Asp Tyr Ala Arg
        195                 200                 205

Gln Ala Gly His His Glu Leu Ala Glu Arg Leu Val Glu Cys Gln Tyr
    210                 215                 220

Glu Leu Thr Asp Arg Leu Ala Phe Tyr Leu Cys Gly Arg Lys Pro Asp
225                 230                 235                 240

His Lys Asn Gly His Tyr Ile Ile Pro Gln Met Ala Asp Ser Leu Asp
                245                 250                 255
```

```
Leu Ser Glu Leu Ala Lys Ala Ala Lys Lys Leu Gln Ala Leu Ser
            260                 265                 270

Asn Arg Leu Phe Glu Glu Leu Ala Met Asp Val Tyr Asp Glu Val Asp
        275                 280                 285

Arg Arg Glu Asn Asp Ala Val Trp Leu Ala Thr Gln Asn His Ser Thr
    290                 295                 300

Leu Val Thr Glu Arg Ser Ala Val Pro Phe Leu Pro Val Asn Pro Glu
305                 310                 315                 320

Tyr Ser Ala Thr Arg Asn Gln Gly Arg Gln Lys Leu Ala Arg Phe Asn
                325                 330                 335

Ala Arg Glu Phe Ala Thr Leu Ile Ile Asp Ile Leu Ser Glu Ala Lys
            340                 345                 350

Arg Arg Gln Gln Gly Lys Ser Leu Ser Ser Pro Thr Asp Asn Leu Glu
        355                 360                 365

Leu Ser Leu Arg Ser Gln Ser Asp Leu Asp Asp Gln His Asp Tyr Asp
    370                 375                 380

Ser Val Ala Ser Asp Glu Asp Thr Asp Gln Glu Pro Leu Arg Ser Thr
385                 390                 395                 400

Gly Ala Thr Arg Ser Asn Arg Ala Arg Ser Met Asp Ser Ser Asp Leu
                405                 410                 415

Ser Asp Gly Ala Val Thr Leu Gln Glu Tyr Leu Glu Leu Lys Lys Ala
            420                 425                 430

Leu Ala Thr Ser Glu Ala Lys Val Gln Gln Leu Met Lys Val Asn Ser
        435                 440                 445

Ser Leu Ser Asp Glu Leu Arg Arg Leu Gln Arg Glu Ile His Lys Leu
    450                 455                 460

Gln Ala Glu Asn Leu Gln Leu Arg Gln Pro Gly Pro Val Pro Thr
465                 470                 475                 480

Pro Pro Leu Pro Ser Glu Arg Ala Glu His Thr Pro Met Ala Pro Gly
                485                 490                 495

Gly Ser Thr His Arg Arg Asp Arg Gln Ala Phe Ser Met Tyr Glu Pro
            500                 505                 510

Gly Ser Ala Leu Lys Pro Phe Gly Gly Pro Pro Gly Asp Glu Leu Thr
        515                 520                 525

Thr Arg Leu Gln Pro Phe His Ser Thr Glu Leu Glu Asp Asp Ala Ile
    530                 535                 540

Tyr Ser Val His Val Pro Ala Gly Leu Tyr Arg Ile Arg Lys Gly Val
545                 550                 555                 560

Ser Ala Ser Ala Val Pro Phe Thr Pro Ser Ser Pro Leu Leu Ser Cys
                565                 570                 575

Ser Gln Glu Gly Ser Arg His Thr Ser Lys Leu Ser Arg His Gly Ser
            580                 585                 590

Gly Ala Asp Ser Asp Tyr Glu Asn Thr Gln Ser Gly Asp Pro Leu Leu
        595                 600                 605

Gly Leu Glu Gly Lys Arg Phe Leu Glu Leu Gly Lys Glu Glu Asp Phe
    610                 615                 620

His Pro Glu Leu Glu Ser Leu Asp Gly Asp Leu Asp Pro Gly Leu Pro
625                 630                 635                 640

Ser Thr Glu Asp Val Ile Leu Lys Thr Glu Gln Val Thr Lys Asn Ile
                645                 650                 655

Gln Glu Leu Leu Arg Ala Ala Gln Glu Phe Lys His Asp Ser Phe Val
            660                 665                 670

Pro Cys Ser Glu Lys Ile His Leu Ala Val Thr Glu Met Ala Ser Leu
```

```
                675                 680                 685

Phe Pro Lys Arg Pro Ala Leu Glu Pro Val Arg Ser Ser Leu Arg Leu
    690                 695                 700

Leu Asn Ala Ser Ala Tyr Arg Leu Gln Ser Glu Cys Arg Lys Thr Val
705                 710                 715                 720

Pro Pro Glu Pro Gly Ala Pro Val Asp Phe Gln Leu Leu Thr Gln Gln
                725                 730                 735

Val Ile Gln Cys Ala Tyr Asp Ile Ala Lys Ala Ala Lys Gln Leu Val
            740                 745                 750

Thr Ile Thr Thr Arg Glu Lys Lys Gln
        755                 760

<210> SEQ ID NO 2
<211> LENGTH: 98
<212> TYPE: PRT
<213> ORGANISM: artificial
<220> FEATURE:
<223> OTHER INFORMATION: ankyrin repeat domain of human GIT1,
      corresponding to aa131-228 of SEQ ID NO: 1

<400> SEQUENCE: 2

Lys Asp Leu Ser Lys Gln Leu His Ser Ser Val Arg Thr Gly Asn Leu
1               5                   10                  15

Glu Thr Cys Leu Arg Leu Leu Ser Leu Gly Ala Gln Ala Asn Phe Phe
            20                  25                  30

His Pro Glu Lys Gly Thr Thr Pro Leu His Val Ala Ala Lys Ala Gly
        35                  40                  45

Gln Thr Leu Gln Ala Glu Leu Val Val Tyr Gly Ala Asp Pro Gly
    50                  55                  60

Ser Pro Asp Val Asn Gly Arg Thr Pro Ile Asp Tyr Ala Arg Gln Ala
65                  70                  75                  80

Gly His His Glu Leu Ala Glu Arg Leu Val Glu Cys Gln Tyr Glu Leu
                85                  90                  95

Thr Asp

<210> SEQ ID NO 3
<211> LENGTH: 97
<212> TYPE: PRT
<213> ORGANISM: artificial
<220> FEATURE:
<223> OTHER INFORMATION: ankyrin repeat domain of GIT1 from Mus
      musculus

<400> SEQUENCE: 3

Asp Leu Ser Lys Gln Leu His Ser Ser Val Arg Thr Gly Asn Leu Glu
1               5                   10                  15

Thr Cys Leu Arg Leu Leu Ser Leu Gly Ala Gln Ala Asn Phe Phe His
            20                  25                  30

Pro Glu Lys Gly Thr Thr Pro Leu His Val Ala Ala Lys Ala Gly Gln
        35                  40                  45

Thr Leu Gln Ala Glu Leu Val Val Tyr Gly Ala Asp Pro Gly Ser
    50                  55                  60

Pro Asp Val Asn Gly Arg Thr Pro Ile Asp Tyr Ala Arg Gln Ala Gly
65                  70                  75                  80

His His Glu Leu Ala Glu Arg Leu Val Glu Cys Gln Tyr Glu Leu Thr
                85                  90                  95

Asp
```

<210> SEQ ID NO 4
<211> LENGTH: 97
<212> TYPE: PRT
<213> ORGANISM: artificial
<220> FEATURE:
<223> OTHER INFORMATION: ankyrin repeat domain of GIT1 from Rattus
      norvegicus

<400> SEQUENCE: 4

Asp Leu Ser Lys Gln Leu His Ser Ser Val Arg Thr Gly Asn Leu Glu
1               5                   10                  15

Thr Cys Leu Arg Leu Leu Ser Leu Gly Ala Gln Ala Asn Phe Phe His
                20                  25                  30

Pro Glu Lys Gly Thr Thr Pro Leu His Val Ala Ala Lys Ala Gly Gln
            35                  40                  45

Thr Leu Gln Ala Glu Leu Leu Val Val Tyr Gly Ala Asp Pro Gly Ser
        50                  55                  60

Pro Asp Val Asn Gly Arg Thr Pro Ile Asp Tyr Ala Arg Gln Ala Gly
65                  70                  75                  80

His His Glu Leu Ala Glu Arg Leu Val Glu Cys Gln Tyr Glu Leu Thr
                85                  90                  95

Asp

<210> SEQ ID NO 5
<211> LENGTH: 97
<212> TYPE: PRT
<213> ORGANISM: artificial
<220> FEATURE:
<223> OTHER INFORMATION: ankyrin repeat domain of GIT1 from Gallus
      gallus

<400> SEQUENCE: 5

Asp Leu Ser Lys Gln Leu His Ser Ser Val Arg Thr Gly Asn Leu Glu
1               5                   10                  15

Thr Cys Leu Arg Leu Leu Ser Leu Gly Ala Gln Ala Asn Phe Phe His
                20                  25                  30

Pro Glu Lys Gly Thr Thr Pro Leu His Val Ala Ala Lys Ala Gly Gln
            35                  40                  45

Ile Leu Gln Ala Glu Leu Leu Val Val Tyr Gly Ala Asp Pro Gly Ala
        50                  55                  60

Pro Asp Val Asn Gly Arg Thr Pro Ile Asp Tyr Ala Arg Gln Ala Ala
65                  70                  75                  80

Gln His Glu Leu Ala Glu Arg Leu Val Glu Cys Gln Tyr Glu Leu Thr
                85                  90                  95

Asp

<210> SEQ ID NO 6
<211> LENGTH: 97
<212> TYPE: PRT
<213> ORGANISM: artificial
<220> FEATURE:
<223> OTHER INFORMATION: ankyrin repeat domain of GIT1 from Camelus
      dromedarius

<400> SEQUENCE: 6

Glu Leu Ser Arg Gln Leu His Ala Ser Val Arg Thr Ser Asn Leu Glu
1               5                   10                  15

Thr Ser Leu Arg Phe Leu Val Gln Gly Ala Asp Pro Asn Tyr Tyr His
                20                  25                  30

Glu Asp Lys Leu Ser Thr Pro Leu His Met Ala Ala Lys Phe Gly Gln
             35                  40                  45

Ala Ser Gln Ile Glu Met Leu Leu Ile Tyr Gly Ala Asp Val Asn Ala
 50                  55                  60

Leu Asp Gly Asn Gly Met Thr Pro Leu Glu Leu Ala Arg Ala Asn Asn
65                  70                  75                  80

His Asn Thr Ile Ala Glu Arg Leu Leu Asp Ala Met Tyr Asp Val Thr
                 85                  90                  95

Asp

<210> SEQ ID NO 7
<211> LENGTH: 97
<212> TYPE: PRT
<213> ORGANISM: artificial
<220> FEATURE:
<223> OTHER INFORMATION: Consensus sequence for ankyrin repeat domain of
      GIT1
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid
<220> FEATURE:
<221> NAME/KEY: misc_feature
<222> LOCATION: (27)..(28)
<223> OTHER INFORMATION: Xaa can be any naturally occurring amino acid
<220> FEATURE:
<221> NAME/KEY: misc_feature
<222> LOCATION: (30)..(31)
<223> OTHER INFORMATION: Xaa can be any naturally occurring amino acid
<220> FEATURE:
<221> NAME/KEY: misc_feature
<222> LOCATION: (33)..(34)
<223> OTHER INFORMATION: Xaa can be any naturally occurring amino acid
<220> FEATURE:
<221> NAME/KEY: misc_feature
<222> LOCATION: (36)..(37)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (49)..(50)
<223> OTHER INFORMATION: Xaa can be any naturally occurring amino acid
<220> FEATURE:

<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (62)..(65)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (73)..(75)
<223> OTHER INFORMATION: Xaa can be any naturally occurring amino acid
<220> FEATURE:
<221> NAME/KEY: misc_feature
<222> LOCATION: (78)..(84)
<223> OTHER INFORMATION: Xaa can be any naturally occurring amino acid
<220> FEATURE:
<221> NAME/KEY: misc_feature
<222> LOCATION: (89)..(92)
<223> OTHER INFORMATION: Xaa can be any naturally occurring amino acid
<220> FEATURE:
<221> NAME/KEY: misc_feature
<222> LOCATION: (94)..(95)
<223> OTHER INFORMATION: Xaa can be any naturally occurring amino acid

<400> SEQUENCE: 7

Xaa Leu Ser Xaa Gln Leu His Xaa Ser Val Arg Thr Xaa Asn Leu Glu
1               5                   10                  15

Thr Xaa Leu Arg Xaa Leu Xaa Xaa Gly Ala Xaa Xaa Asn Xaa Xaa His
            20                  25                  30

Xaa Xaa Lys Xaa Xaa Thr Pro Leu His Xaa Ala Ala Lys Xaa Gly Gln
        35                  40                  45

Xaa Xaa Gln Xaa Glu Xaa Leu Xaa Xaa Tyr Gly Ala Asp Xaa Xaa Xaa
    50                  55                  60

Xaa Asp Xaa Asn Gly Xaa Thr Pro Xaa Xaa Ala Arg Xaa Xaa Xaa
65                  70                  75                  80

Xaa Xaa Xaa Xaa Ala Glu Arg Leu Xaa Xaa Xaa Xaa Tyr Xaa Xaa Thr
                85                  90                  95

Asp

<210> SEQ ID NO 8
<211> LENGTH: 97
<212> TYPE: PRT
<213> ORGANISM: artificial
<220> FEATURE:
<223> OTHER INFORMATION: Consensus sequence for ankyrin repeat domain of
      GIT1
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:

-continued

```
<221> NAME/KEY: misc_feature
<222> LOCATION: (80)..(81)
<223> OTHER INFORMATION: Xaa can be any naturally occurring amino acid

<400> SEQUENCE: 8

Asp Leu Ser Lys Gln Leu His Ser Ser Val Arg Thr Gly Asn Leu Glu
1               5                   10                  15

Thr Cys Leu Arg Leu Leu Ser Leu Gly Ala Gln Ala Asn Phe Phe His
            20                  25                  30

Pro Glu Lys Gly Thr Thr Pro Leu His Val Ala Ala Lys Ala Gly Gln
        35                  40                  45

Xaa Leu Gln Ala Glu Leu Leu Val Val Tyr Gly Ala Asp Pro Gly Xaa
50                  55                  60

Pro Asp Val Asn Gly Arg Thr Pro Ile Asp Tyr Ala Arg Gln Ala Xaa
65                  70                  75                  80

Xaa His Glu Leu Ala Glu Arg Leu Val Glu Cys Gln Tyr Glu Leu Thr
                85                  90                  95

Asp

<210> SEQ ID NO 9
<211> LENGTH: 180
<212> TYPE: DNA
<213> ORGANISM: artificial
<220> FEATURE:
<223> OTHER INFORMATION: human GIT1, ankyrin repeat domain-encoding
      fragment

<400> SEQUENCE: 9
aaagatctga gcaaacagct gcatagcagc gtgcgcaccg gcaacctgga aacctgcctg      60
cgcctgctga gcctgggcgc gcaggcgaac ttttttcatc cggaaaaagg caccaccccg     120
ctgcatgtgg cggcgaaagc gggccagacc ctgcaggcgg aactgctggt ggtgtatggc     180

<210> SEQ ID NO 10
<211> LENGTH: 180
<212> TYPE: DNA
<213> ORGANISM: artificial
<220> FEATURE:
<223> OTHER INFORMATION: consensus ankyrin repeat domain-encoding
      fragment
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
```

-continued

```
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t
<220> FEATURE:
<221> NAME/KEY: misc_feature
<222> LOCATION: (117)..(117)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (123)..(123)
<223> OTHER INFORMATION: n is a, c, g, or t
<220> FEATURE:
<221> NAME/KEY: misc_feature
<222> LOCATION: (129)..(129)
```

<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t

<400> SEQUENCE: 10
aargayytnw snaarcaryt ncaywsnwsn gtnmgncang gnaayytnga rcantgyytn 60
mgnytnytnw snytnggngc ncargcnaay ttyttycayc cngaraargg ncancanccn 120
ytncaygtng cngcnaargc nggncarcan ytncargcng arytnytngt ngtntayggn 180

<210> SEQ ID NO 11
<211> LENGTH: 5
<212> TYPE: PRT
<213> ORGANISM: artificial
<220> FEATURE:
<223> OTHER INFORMATION: endothelial cell-targeting peptide

<400> SEQUENCE: 11

Pro His Ser Arg Asn
1 5

<210> SEQ ID NO 12
<211> LENGTH: 5
<212> TYPE: PRT
<213> ORGANISM: artificial
<220> FEATURE:
<223> OTHER INFORMATION: endothelial cell-targeting peptide

```
<400> SEQUENCE: 12

Tyr Ile Gly Ser Arg
1               5

<210> SEQ ID NO 13
<211> LENGTH: 4
<212> TYPE: PRT
<213> ORGANISM: artificial
<220> FEATURE:
<223> OTHER INFORMATION: endothelial cell-targeting peptide

<400> SEQUENCE: 13

His Trp Gly Phe
1

<210> SEQ ID NO 14
<211> LENGTH: 7
<212> TYPE: PRT
<213> ORGANISM: artificial
<220> FEATURE:
<223> OTHER INFORMATION: linker sequence

<400> SEQUENCE: 14

Gly Ser Gly Gly Ser Gly Ser
1               5

<210> SEQ ID NO 15
<211> LENGTH: 5
<212> TYPE: PRT
<213> ORGANISM: artificial
<220> FEATURE:
<223> OTHER INFORMATION: linker sequence

<400> SEQUENCE: 15

Gly Ser Gly Ser Gly
1               5

<210> SEQ ID NO 16
<211> LENGTH: 5
<212> TYPE: PRT
<213> ORGANISM: artificial
<220> FEATURE:
<223> OTHER INFORMATION: ankyrin repeat domain sequence

<400> SEQUENCE: 16

Thr Thr Pro Leu His
1               5

<210> SEQ ID NO 17
<211> LENGTH: 48
<212> TYPE: PRT
<213> ORGANISM: artificial
<220> FEATURE:
<223> OTHER INFORMATION: SHD inhibitor peptide

<400> SEQUENCE: 17

Asp Leu Ser Glu Leu Ala Lys Ala Ala Lys Lys Leu Gln Ala Leu
1               5                   10                  15

Ser Asn Arg Leu Phe Glu Glu Leu Ala Met Asp Val Tyr Asp Glu Val
                20                  25                  30

Asp Arg Arg Glu Asn Asp Ala Val Trp Leu Ala Thr Gln Asn His Ser
            35                  40                  45

<210> SEQ ID NO 18
<211> LENGTH: 17
```

```
<212> TYPE: PRT
<213> ORGANISM: artificial
<220> FEATURE:
<223> OTHER INFORMATION: SHD inhibitor peptide

<400> SEQUENCE: 18

Asp Gln His Asp Tyr Asp Ser Val Ala Ser Asp Glu Asp Thr Asp Gln
1               5                   10                  15

Glu

<210> SEQ ID NO 19
<211> LENGTH: 27
<212> TYPE: DNA
<213> ORGANISM: artificial
<220> FEATURE:
<223> OTHER INFORMATION: primer

<400> SEQUENCE: 19
tacagtgtgg aaatgggaag tgaaagc                                      27

<210> SEQ ID NO 20
<211> LENGTH: 24
<212> TYPE: DNA
<213> ORGANISM: artificial
<220> FEATURE:
<223> OTHER INFORMATION: primer

<400> SEQUENCE: 20
ggagaaggtg ccaggaaggc ttta                                         24

<210> SEQ ID NO 21
<211> LENGTH: 21
<212> TYPE: DNA
<213> ORGANISM: artificial
<220> FEATURE:
<223> OTHER INFORMATION: GIT1 siRNA target

<400> SEQUENCE: 21
aagctgccaa gaagaagcta c                                            21

<210> SEQ ID NO 22
<211> LENGTH: 21
<212> TYPE: DNA
<213> ORGANISM: artificial
<220> FEATURE:
<223> OTHER INFORMATION: control, non-silencing siRNA target

<400> SEQUENCE: 22
aattctccga cacgtgtcac t                                            21

<210> SEQ ID NO 23
<211> LENGTH: 24
<212> TYPE: DNA
<213> ORGANISM: artificial
<220> FEATURE:
<223> OTHER INFORMATION: primer D114 (mouse)

<400> SEQUENCE: 23
ccgcatttgc cttaagcact tcca                                         24

<210> SEQ ID NO 24
<211> LENGTH: 24
<212> TYPE: DNA
<213> ORGANISM: artificial
<220> FEATURE:
<223> OTHER INFORMATION: primer D114 (mouse)
```

```
<400> SEQUENCE: 24
aaattgaagg gcaactgcag aggg                                              24

<210> SEQ ID NO 25
<211> LENGTH: 24
<212> TYPE: DNA
<213> ORGANISM: artificial
<220> FEATURE:
<223> OTHER INFORMATION: primer Dll4 (human)

<400> SEQUENCE: 25
cctgcattgt gaacacagca cctt                                              24

<210> SEQ ID NO 26
<211> LENGTH: 24
<212> TYPE: DNA
<213> ORGANISM: artificial
<220> FEATURE:
<223> OTHER INFORMATION: primer Dll4 (human)

<400> SEQUENCE: 26
acctgtccac tttcttctcg cagt                                              24

<210> SEQ ID NO 27
<211> LENGTH: 24
<212> TYPE: DNA
<213> ORGANISM: artificial
<220> FEATURE:
<223> OTHER INFORMATION: primer HEY1 (mouse)

<400> SEQUENCE: 27
gaaacttgag ttcggcgctg tgtt                                              24

<210> SEQ ID NO 28
<211> LENGTH: 24
<212> TYPE: DNA
<213> ORGANISM: artificial
<220> FEATURE:
<223> OTHER INFORMATION: primer HEY1 (mouse)

<400> SEQUENCE: 28
agatccctgc ttctcaaagg cact                                              24

<210> SEQ ID NO 29
<211> LENGTH: 24
<212> TYPE: DNA
<213> ORGANISM: artificial
<220> FEATURE:
<223> OTHER INFORMATION: primer HEY1 (human)

<400> SEQUENCE: 29
agagtgcgga cgagaatgga aact                                              24

<210> SEQ ID NO 30
<211> LENGTH: 24
<212> TYPE: DNA
<213> ORGANISM: artificial
<220> FEATURE:
<223> OTHER INFORMATION: primer HEY1 (human)

<400> SEQUENCE: 30
accagccttc tcagctcaga caaa                                              24

<210> SEQ ID NO 31
```

```
<211> LENGTH: 13
<212> TYPE: PRT
<213> ORGANISM: artificial
<220> FEATURE:
<223> OTHER INFORMATION: ANK-Active ANK peptide

<400> SEQUENCE: 31

Gly Thr Thr Pro Leu His Val Ala Ala Lys Ala Gly Gln
1               5                   10

<210> SEQ ID NO 32
<211> LENGTH: 12
<212> TYPE: PRT
<213> ORGANISM: artificial
<220> FEATURE:
<223> OTHER INFORMATION: sANK-Scrambled ANK peptide

<400> SEQUENCE: 32

Thr Leu Gln Ala Glu Leu Leu Val Val Tyr Gly Ala
1               5                   10

<210> SEQ ID NO 33
<211> LENGTH: 11
<212> TYPE: PRT
<213> ORGANISM: artificial
<220> FEATURE:
<223> OTHER INFORMATION: HIV-1 TAT sequence

<400> SEQUENCE: 33

Tyr Gly Arg Lys Lys Arg Arg Gln Arg Arg Arg
1               5                   10
```